(12) United States Patent
Kiessling et al.

(10) Patent No.: US 9,861,702 B2
(45) Date of Patent: Jan. 9, 2018

(54) LIPID-CONJUGATED RHAMNOSE FOR IMMUNE SYSTEM RECRUITMENT AND ONCOTHERAPY

(71) Applicant: WISCONSIN ALUMNI RESEARCH FOUNDATION, Madison, WI (US)

(72) Inventors: Laura L. Kiessling, Madison, WI (US); Rachael T. C. Sheridan, Madison, WI (US); Jonathan Hudon, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 360 days.

(21) Appl. No.: 13/842,800

(22) Filed: Mar. 15, 2013

(65) Prior Publication Data

US 2014/0112975 A1 Apr. 24, 2014

Related U.S. Application Data

(60) Provisional application No. 61/717,079, filed on Oct. 22, 2012.

(51) Int. Cl.
*A61K 47/48* (2006.01)
*A61K 47/54* (2017.01)

(52) U.S. Cl.
CPC ...... *A61K 47/48046* (2013.01); *A61K 47/543* (2017.08); *A61K 47/544* (2017.08)

(58) Field of Classification Search
None
See application file for complete search history.

(56) References Cited

U.S. PATENT DOCUMENTS

| | | | |
|---|---|---|---|
| 5,466,675 A | 11/1995 | Piljac et al. | |
| 5,525,709 A | 6/1996 | Davey et al. | |
| 5,610,040 A | 3/1997 | Smeets et al. | |
| 5,665,778 A | 9/1997 | Semeria et al. | |
| 5,879,675 A | 3/1999 | Galili et al. | |
| 6,071,532 A | 6/2000 | Chaikof et al. | |
| 6,171,614 B1 | 1/2001 | Chaikof et al. | |
| 6,228,985 B1 | 5/2001 | Blood et al. | |
| 6,361,775 B1 | 3/2002 | Galili et al. | |
| 7,344,868 B2 | 3/2008 | Lassalle | |
| 7,772,380 B2 | 8/2010 | Porcelli | |
| 7,820,628 B2 * | 10/2010 | Galili | 514/25 |
| 8,022,043 B2 | 9/2011 | Porcelli | |
| 2009/0081148 A1 | 3/2009 | Cannell et al. | |
| 2010/0104585 A1 | 4/2010 | Kiessling et al. | |

FOREIGN PATENT DOCUMENTS

EP 0 612 527 8/1994

OTHER PUBLICATIONS

Chen, L-rhamnose antigen, a promising alterative to alpha gal for cancer immunotherapies, ACS Chem, Biol, 2011, 6, 184-191.*
Siegel, Effect of influenza hemagglutinin fusion peptide on lamellar/inverted phase transitions in dipalmitoleoylphosphatidylethanolamine, Biochimica et Biophysica Acta, 1468, 2000, 87-98.*
Alberts B, Molecular Biology of the Cell, 4th edition, New York: Garland Science, 2002.*
Abu-Baker et al. (Jul. 16, 2012) "Design of Fully Synthetic, Self-Adjuvanting Vaccine Incorporating the Tumor-Associated Carbohydrate Tn Antigen and Lipoamino Acid-Based Toll-like Receptor 2 Ligand," *J. Medicinal Chem.* 55(15):6968-6974.
Agnihotri et al. (Dec. 2011) "Structure—Activity Relationships in Toll-Like Receptor 2-Agonists Leading to Simplified Monoacyl Lipopeptides," *J. Med. Chem.* 54(23):8148-8160.
Bentley et al. (2006) "Genetic Analysis of the Capsular Biosynthetic Locus from All 90 Pneumococcal Serotypes," PLoS Genetics. 2(3):e31.
Berd (2001) "Autologous, hapten-modified vaccine as a treatment for human cancers," *Vaccine.* 19:2565-2570.
Bryant et al. (1993) "Six monoclonal antibodies to the CD59 antigen," *Immunohematology.* 9(3):68-73.
Buskas et al. (2005) "Towards a Fully Synthetic Carbohydrate-Based Anticancer Vaccine: Synthesis and Immunological Evaluation of a Lipidated Glycopeptide Containing the Tumor-Associated Tn Antigen," *Angew. Chem. Int. Ed.* 44:5985-5988.
Carlson et al. (2007) *ACS Chem. Biol.* 2:119-127.
Chen et al. (Nov. 2, 2010) "$_L$-Rhamnose Antigen: A Promising Alternative to α-Gal for Cancer Immunotherapies," *ACS Chem. Biol.* 6:185-191.
Copper (Jul. 2002) "Optical biosensors in drug discovery," *Nature Reviews Drug Discovery.* 1:515-528.
Courtney et al. (2009) "Sialylated multivalent antigens engage CD22 in trans and inhibit B cell activation," *Proc. Natl. Acad. Sci. U.S.A.* 106(8):2500-2505.
Davis (1999) "Recent Developments in Glycoconjugates," *J. Chem. Soc., Perkin Trans.* 1:3215-3237.
Deriy et al. (Jun. 2005) "In vivo targeting of vaccinating tumor cells to antigen-presenting cells by a gene therapy method with adenovirus containing the alpha 1,3-galactosyltransferase gene," *Cancer Gene Ther.* 12(6):528-39.

(Continued)

*Primary Examiner* — Celeste A Roney
(74) *Attorney, Agent, or Firm* — Lathrop Gage LLP

(57) ABSTRACT

L-Rhamnose antigen-lipid conjugates for recruitment of the immune system to sites of tumor growth for initiating an anti-tumor antigen response. Methods for introducing L-rhamnose antigen-conjugated lipids into cell membranes such that L-rhamnose antigens are displayed on the cell surface. The cells can be tumor cells and more specifically can be melanoma cells. Cells are contacted with one or more L-rhamnose antigen-lipid conjugates such that L-rhamnose antigen-lipid conjugates are inserted into the cell membrane. The cells can be contacted for example by intratumoral injection. Pharmaceutical compositions containing the L-rhamnose antigen-lipid conjugates and therapeutic methods employing the conjugates and compositions.

14 Claims, 9 Drawing Sheets

(56) References Cited

OTHER PUBLICATIONS

DiGaetano et al. (Sep. 2001) "Synergism between fludarabine and rituximab revealed in a follicular lymphoma cell line resistant to the cytotoxic activity of either drug alone," *J. Haematol.* 114(4):800-809.
Dubrovska et al. (Sep. 21, 2011) "A Chemically Induced Vaccine Strategy for Prostate Cancer," *ACS Chemical Biology.* 6(11):1223-1231.
Fletcher et al. (1992) "New monoclonal antibodies in CD59: use for the analysis of peripheral blood cells from paroxysmal nocturnal haemoglobinuria (PNH) patients and for the quantitation of CD59 on normal and decay accelerating factor (DAF)-deficient erythrocytes," *Immunology.* 75(3):507-512.
Galili (2001) "The α-Gal epitope (Galα1-3Galβ1-4GlcNAc-R) in xenotransplantation," *Biochemie.* 83:557-563.
Galili (May 4, 2010) "In Situ Conversion of Melanoma Lesions into Autologous Vaccine by Intratumoral Injections of α-Gal Glycolipids," *Cancers.* 2:773-793.
Galili (published online Jun. 16, 2004) "Autologous tumor vaccines processed to express alpha-gal epitopes: A practical approach to immunotherapy in cancer," *Cancer Immunol Immunother.* 53(11):935-45.
Galili et al. (1984) "A unique natural human IgG antibody with anti-alpha-galactosyl specificity," *J. Exp. Med.* 160:1519-1531.
Galili et al. (2007) "Intratumoral Injection of α-Gal Glycolipids Induces Xenograft-Like Destruction and Conversion of Lesions into Endogenous Vaccines," *J. Immunology.* 178:4676-4687.
Gelderman et al. (2004) "Complement Function in mAb-mediated Cancer Immunotherapy," *Trends Immunology.* 25:158-164.
Gillies et al. (1999) "Improving the efficacy of antibody-interleukin 2 fusion proteins by reducing their interaction with Fc receptors," *Cancer Research.* 59(9):2159-66.
Gruber et al. (Jul. 2012) "Development and clinical evaluation of Prevnar 13, a 13-valent pneumococcocal CRM(197) conjugate vaccine," *Annals of the New York Academy of Sciences.* 1263:15-26.
Huflejt et al. (2009) "Anti-carbohydrate antibodies of normal sera: findings, surprises and challenges," *Mol. Immunol.* 46:3037-3049.
Klim et al. (Dec. 27, 2011) "Small-Molecule-Modified Surfaces Engage Cells through the $\alpha_v\beta_3$ Integrin," *ACS Chemical Biology.* 7:518-525.
Klok et al. (2002) "Self-Assembling Biomaterials: I-Lysine-Dendron-Substituted Cholesteryl-(l-lactic acid)$_n$," *Macromolecules.* 35(16):6101-611.
Liu et al. (2005) "The complement inhibitory protein DAF (CD55) suppresses T cell immunity in vivo," *JEM.* (4):567-577.
Liu et al. (Jun. 17, 2011) "Membrane Anchored Immunostimulatory Oligonucleotides for In Vivo Cell Modification and Localized Immunotherapy," *Angew. Chem. Int. Ed. Engl.* 123:7190-7193.
Liu et al. (Jun. 17, 2011) "Membrane Anchored Immunostimulatory Oligonucleotides for In Vivo Cell Modification and Localized Immunotherapy," *Angew. Chem. Int. Ed. Engl.* 50(31):7052-7055.
Llinas et al. (2005) "Crystal structure of the human urokinase plasminogen activator receptor bound to an antagonist peptide," *The EMBO Journal.* 24:1655-1663.
Lu et al. (2002) "Folate targeting of haptens to cancer cell surfaces mediates immunotherapy of syngeneic murine tumors," *Cancer Immunol Immunother.* 51:153-162.

Manches et al. (2005) "Anti-Gal-Mediated Targeting of Human B Lymphoma Cells to Antigen-Presenting Cells: A Potential Method for Immunotherapy Using Autologous Tumor Cells," *The Hematology Journal.* 90(5):625-634.
Mata-Haro et al. (2007) "The Vaccine Adjuvant Monophosphoryl Lipid A as a TRIF-Biased Agonist of TLR4," *Science.* 316(5831):1628-1632.
Murelli et al. (Dec. 2, 2009) "Chemical Control Over Immune Recognition: A Class of Antibody-Recuiting Small Molecules (ARMs) that Target Prostate Cancer," *J. Am. Chem. Soc.* 131:17090-17092.
Niehans et al. (Jul. 1996) "Human carcinomas variably express the complement inhibitory proteins CD46 (membrane cofactor protein), CD55 (decay-accelerating factor), and CD59 (protectin)," *Am J. Pathology* 149(1):129-142.
Owen et al. (2007) "Bifunctional ligands that target cells displaying the $\alpha_v\beta_3$ integrin," *Chembiochem.* 8(1):68-82.
Oyelaran et al. (Sep. 2009) "Profiling Human Serum Antibodies with a Carbohydrate Antigen Microarray," *J. Proteome Res.* 8:4301-4310.
Pazur et al. (1983) "Isomeric, Anti-Rhamnose Antibodies Having Specificity for Rhamnose-Containing, Streptococcal Heteroglycans," *Carbohydrate Research.* 124:253-263.
Popkov et al. (2009) "Instant immunity through chemically programmable vaccination and covalent self-assembly," *Proc. Natl. Acad. Sci. U.S.A.* 106:4378-4383.
Robson et al. (1994) "6-Hydroxy-4-Sphingenine in Human Epidermal Ceramides," *Journal of Lipid Research.* 35:2060-2068.
Sarkar et al. (Nov. 2010) "Synthesis of a Single-Molecule l-Rhamnose-Containing Three-Component Vaccine and Evaluation of Antigenicity in the Presence of Anti-l-Rhamnose Antibodies," *J. Am. Chem. Soc.* 132(48):17236-17246.
Sheridan RT, Hudon J, Hank JA, Sondel PM, Kiessling LL. Rhamnose glycoconjugates for the recruitment of endogenous anticarbohydrate antibodies to tumor cells. Chembiochem. Jul. 7, 2014;15(10):1393-8.
Wang et al. (Oct. 20, 2011) "Carbohydrate-Monophosphoryl Lipid A Conjugates Are Fully Synthetic Self-Adjuvanting Cancer Vaccines Eliciting Robust Immune Responses in the Mouse," *ACS Chem. Biol.* 7(1):235-240.
Wiselander et al. (1990) "Specificity of human antibodies against galα1-3gal carbohydrate epitope and distinction from natural antibodies reacting with galα1-2gal or galα1-4 gal," *Glycoconjugate Journal.* 7(1):85-100.
Wu et al. (Mar. 19, 2010) "Structure-activity relationships in toll-like receptor-2 agonistic diacylthioglycerol lipopeptides," *J. Med. Chem.* 53:3198-3213.
Sarkar, S., Talan, R S., Lombardo, S. A, Wall, K. A, Sucheck, S.J. (2010) Synthesis of a single molecule L-rhamnose-containing three component vaccine and evaluation of antigenicity in the presence of anti L-rhamnose antibodies, Abstracts of Papers, 240th National Meeting of the American Chemical Society, Boston, MA, Aug. 22-26, 2010, American Chemical Society, Washington, DC, CARB-17.
Long, D.E. et al., Synthesis of -L-Rhamnosyl Ceramide and Evaluation of its Binding with Anti-Rhamnose Antibodies, Author manuscript; Bioorg Med Chem. Oct. 1, 2015; 22(19): 5279-5289.

\* cited by examiner

LIPID-CONJUGATED RHAMNOSE FOR IMMUNE SYSTEM RECRUITMENT AND ONCOTHERAPY

CROSS-REFERENCE TO RELATED APPLICATIONS

This application claims the benefit of U.S. provisional application 61/717,079, filed Oct. 22, 2012 which is incorporated by reference herein in its entirety.

STATEMENT REGARDING GOVERNMENT FUNDING

This invention was made with government support under W81XWH-08-1-0648 awarded by the ARMY/MRMC. The government has certain rights in the invention.

BACKGROUND OF THE INVENTION

Recruitment of the immune system to sites of tumor growth for the purpose of initiating an anti-tumor antigen response is a promising approach to cancer treatment. [U. Galili, K. Wigglesworth and U. M. Abdel-Motal, J. Immunology, 2007, 178, 4676-4687; C. B. Carlson, P. Mowery, R. M. Owen, E. C. Dykhuizen and L. L. Kiessling, ACS Chem. Biol., 2007, 2, 119-127; R. P. Murelli, A. X. Zhang, J. Michel, W. L. Jorgensen and D. A. Spiegel, J. Am. Chem. Soc., 2009, 131, 17090-17092; M. Popkov, B. Gonzalez, S. C. Sinha and C. F. Barbas, Proc. Natl. Acad. Sci. USA 2009, 106, 4378-4383.]

The ability to recruit endogenous antibodies to tumor sites allows for clearance of targeted cells through both complement-dependent cytotoxicity (CDC) and antibody-dependent cell-mediated cytotoxicity (ADCC). CDC is promoted primarily by antibodies of the IgM isotype; decoration of cells with sufficient levels of antibody leads to activation of the classical complement cascade to form pores in the target cell membranes and release cytokines which attract immune cells. ADCC is dependent on the activation of NK and other immune effector cells through ligation of their activating Fc receptor (FcγRIII) by IgG antibodies. CDC and ADCC are linked; soluble factors released during complement activation recruit effector cells for ADCC, thus activation of both pathways is beneficial for optimal tumor clearance. In addition to effecting tumor removal, these methods have the potential to prime the immune system to recognize tumor-associated antigens in the future, in essence, forming an in situ autologous vaccine [D. Berd, Vaccine 2001, 19, 2565-2570; U. Galili, M. R. Albertini, P. M. Sondel, K. Wigglesworth, M. Sullivan and G. F. Whalen, Cancers, 2010, 2, 773-793.]

By tagging tumor cells with a widely-recognized foreign antigen, serum antibodies of both IgG and IgM isotype will bind and initiate immune responses leading to both tumor clearance and immune system priming. This approach requires a suitable antigen for antibody recruitment and a method to tag the desired cells.

The ideal antigen for such methods would be recognized by a majority of the target population (e.g., humans) without prior vaccination, and would be able to recruit both IgG and IgM classes. The antigen Gal-α-1,3-Gal (herein called αGal) is recognized as having these properties. This antigen is present in much of nature with the striking exceptions of humans, chimps, and old world monkeys. As such, humans are frequently exposed to this carbohydrate and develop fairly high, stable titers of both IgG and IgM isotypes against it.

One method of cell tagging takes advantage of the propensity of exogenously added lipids to partition into nearby cell membranes. For example, certain αGal lipids were isolated from rabbit erythrocytes and injected intratumorally. The injected lipids were reported to insert into tumor membranes forming a display of antigenic carbohydrates [U. Galili, K. Wigglesworth and U. M. Abdel-Motal, 2007, 178, 4676-4687]. This approach using certain αGal lipids has been reported to be successful in both mouse models and the clinic. See also U.S. Pat. Nos. 7,820,628; 6,361,775; and 5,879,675. A second tagging approach uses small molecules to target upregulated tumor surface receptors. Both αvβ3 integrins and PSMA (prostate-specific membrane antigen) have been targeted in this manner; however, robust cell killing under physiologically relevant conditions has not yet been achieved [C. B. Carlson, P. Mowery, R. M. Owen, E. C. Dykhuizen and L. L. Kiessling, 2007, ACS Chemical Biology 2, 119-127; R. P. Murelli, A. X. Zhang, J. Michel, W. L. Jorgensen and D. A. Spiegel, J. Am. Chem. Soc. 2009, 131, 17090-17092.]

Recent microarray studies profiling human serum antibodies to various carbohydrates have identified rhamnose as a molecule of interest. Anti-rhamnose was reported to be present in a greater number of serum samples, and was reported to be more abundant than anti-Gal [M. E. Huflejt, M. Vuskovic, D. Vasiliu, H. Xu, P. Obukhova, N. Shilova, A. Tuzikov, O. Galanina, B. Arun, K. Lu and N. Bovin, Mol. Immunol. 2009, 46, 3037-3049, O. Oyelaran, L. M. McShane, L. Dodd and J. C. Gildersleeve, J. Proteome Res. 2009, 8, 4301-4310] In addition, it was reported that normal strains of lab mice can be immunized against rhamnose to create a model system without the need for special knockout animals [W. Chen, L. Gu, W. Zhang, E. Motari, L. Cai, T. J. Styslinger and P. G. Wang, ACS Chem. Biol. 2011, 6, 185-191.]

The present invention relates to the use of L-rhamnose antigen-lipid conjugates to recruit anti-L-Rha antibodies to cells to initiate an anti-cell antigen response. In particular, the cells are tumor cells and use of the L-rhamnose antigen-lipid conjugates activates the complement pathway, induces complement-mediated cell death and initiates cell-dependent cytotoxic pathways, such as cytotoxic T cell response.

SUMMARY OF THE INVENTION

The invention provides L-rhamnose antigen-lipid conjugates for recruitment of the immune system to sites of tumor growth for the purpose of initiating an anti-tumor antigen response. In specific embodiments, the L-rhamnose antigen-lipid conjugates comprise two or more L-rhamnose moieties. In an embodiment, the L-rhamnose moieties are L-rhamnose monosaccharides. In an embodiment, the L-rhamnose antigen is two or more L-rhamnose monosaccharides. In another embodiment, the L-rhamnose antigen is an L-rhamnose dimer or oligomer.

In a specific embodiment, the L-rhamnose antigen-lipid conjugates of the invention have structure:

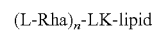

(L-Rha)$_n$-LK-lipid where L-Rha is an L-Rha antigen, n is the number of L-Rha antigens in the conjugate, LK is a divalent or multivalent linker and lipid is a lipid which can insert into a cell membrane. The conjugate contains at least two L-Rha moieties. When the L-Rha antigen is L-rhamnose, n is 2 or more, 2-500, 2-256, 2-100 and more specifically n is 2-64, 2-32, 2-16, 2-8 or 2-4 and yet more specifically 2, 4, 8, 16, 32, 64 or 256. In more specific embodiments, n is 2, 4 or 8. When L-Rha antigen is a dimer or oligomer of 1-rhamnose, n is 1 or more. In specific embodiments, n is 1-10, 1-5, 1, 2, 3, 4 or 5. In specific embodiments, LK is a linker as described below or in the examples herein.

In specific embodiments, the L-rhamnose antigen-lipid conjugates have a structure in which the lipid is generally elongate with a polar head group and a hydrophilic portion, comprising one or two hydrophobic groups, at either end of the lipid and the two or more L-rhamnose moieties are conjugated to the polar head group of the lipid. This structure is believed to be preferred for proper insertion of the L-rhamnose antigen-lipid conjugate into cell membranes. In specific embodiments, lipids are those of formulas PEX, PEX1, PEAX, PEAX1, SphX, SphX1, CerX, or CerX. In specific embodiments, the lipids are glycerolipids, glycerophospholipids, or sphingolipids, including ceramides. More specifically, the lipids are glycerophosphoethanolamines. In these embodiments, the hydrophobic lipid groups are generally composed of saturated, monounsaturated or polyunsaturated straight-chain hydrocarbons or corresponding acyl groups having 6 to 32 carbon atoms, and more typically at least one hydrocarbon group or corresponding acyl group that has 10 or more carbon atoms. The hydrocarbon or corresponding acyl groups can be substituted with one or more methyl groups, typically 1-4 methyl groups, which provide some level of branching. Hydrocarbons chains or corresponding acyl hydrocarbon groups having saturated or unsaturated branches which are greater than 1 carbon in length are not preferred. The hydrocarbon groups or corresponding acyl hydrocarbon groups can be substituted with one or more hydroxyl groups, typically 1-3 hydroxyl groups. Hydrocarbon groups or corresponding acyl hydrocarbon groups may be monounsaturated or may be polyunsaturated. If polyunsaturated, the double bonds in the hydrocarbon or corresponding acyl hydrocarbon can be conjugated or unconjugated. In specific embodiments, polyunsaturated hydrocarbons or corresponding acyl polyunsaturated hydrocarbons of the lipids carry 2-4 double bonds. In specific embodiments, the lipid carries one unsubstituted saturated hydrocarbon or corresponding acyl group and one hydrocarbon or corresponding acyl group that is unsaturated, polyunsaturated or substituted with 1-3 hydroxyl groups or a combination of unsaturation and substitution. In specific embodiments, the lipid carries two monounsaturated hydrocarbon or corresponding acyl groups. In specific embodiments, the lipid carries a straight-chain unsubstituted hydrocarbon or corresponding acyl group and a monounsaturated hydrocarbon or corresponding acyl group. In specific embodiments, the lipid carries a straight-chain unsubstituted hydrocarbon or corresponding acyl group and a polyunsaturated hydrocarbon or corresponding acyl group, particularly where there are 2, 3 or 4 double bonds. In specific embodiments, the lipid carries a hydroxyl-substituted saturated hydrocarbon or corresponding acyl group and a mono- or polyunsaturated hydrocarbon or corresponding acyl group.

Glycerolipids, glycerophospholipids and more specifically glycerophosphoethanolamine lipids, can contain one or two acyl hydrocarbon groups which may be saturated, monounsaturated or polyunsaturated or which may be substituted as noted above with one or more hydroxyl or one or more methyl groups. Glycerolipids, glycerophospholipids and more specifically glycerophosphoethanolamine lipids can contain one or two hydrocarbon groups (bonded to a —O— of the glycerol) which may be saturated, monounsaturated or polyunsaturated or which may be substituted as noted above with one or more hydroxyl or one or more methyl groups. Glycerolipids, glycerophospholipids and more specifically glycerophosphoethanolamine lipids can contain one hydrocarbon group, which may be saturated, monounsaturated or polyunsaturated or which may be substituted as noted above with one or more hydroxyl or one or more methyl groups, and one corresponding acyl hydrocarbon group.

In specific embodiments, the lipids of the L-rhamnose antigen-lipid conjugates are sterols or steroids. In specific embodiments, the lipids are 3-OH sterols. In specific embodiments, the lipid is cholesterol.

The two or more L-rhamnose moieties are conjugated to any lipid that is capable of being inserted into an animal cell membrane, particularly a human cell membrane. In specific embodiments, the lipid is a glycerophosphoethanolamine, a sphingolipid, a ceramide, a sterol or steroid. More specifically, the lipid is DPoPE (dipalmitoleoylphosphatidylethanolamine), a ceramide or cholesterol.

The L-rhamnose antigen-lipid conjugate contains two or more L-rhamnose moieties. In a specific embodiment, the L-rhamnose antigen-lipid conjugate comprises 2-500 L-rhamnose moieties. In specific embodiments, the lipid conjugate comprises 2-256 L-rhamnose moieties. In specific embodiments, the lipid conjugate comprises 2-100 L-rhamnose moieties. In other embodiments, the lipid conjugate comprises 2-32 L-rhamnose moieties. In other embodiments, the lipid conjugate comprises 2-16 L-rhamnose moieties. In other embodiments, the lipid conjugate comprises 2-8 L-rhamnose moieties. In other embodiments, the lipid conjugate comprises 2-4 L-rhamnose moieties. In other embodiments, the lipid conjugate comprises 2, 4, 8, 16 or 32 L-rhamnose moieties. In specific embodiments, the L-rhamnose antigen comprises 16-256 L-rhamnose moieties linked to a dendron or dendrimer structure.

The L-rhamnose antigen-lipid conjugate formally contains 2 or more L-rhamnose moieties linked via a divalent or multivalent linker to a lipid. The linker contains chemical moieties resulting from bonding of the L-rhamnose antigen and from bonding of the lipid as well as an optional spacer. In specific embodiments, the chemical moieties resulting from bonding can be amide moieties (—NH—CO—, —CO—NH—), ester moieties (—O—CO—, —CO—O—), thioester (—S—CO— or —CO—S—), sulfonamide (—SO$_2$—NH—, —NH—SO$_2$—)—O—, —S—, —NH—, or —NH—CO—NH—, among others. In a particular embodiment, the linker between the L-rhamnose moieties and the lipid is created using a Click reaction. In the standard Click reactions an azide group reacts with alkenyl or akynyl groups to form triazolines or triazoles, respectively. Linkers formed in such reactions will include a triazoline or triazole moiety. In specific embodiments, the chemical moieties resulting from bonding can be:

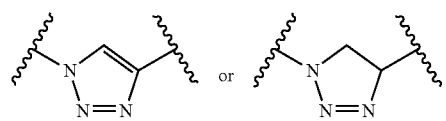 [SMILES: *c1cn(*)nn1 ; *C1CN(*)N=N1]

moieties.

In specific embodiments, the spacer of the linker moiety is an alkylene chain having 1-12, 2-6 or 2-6 carbon atoms which bridges the chemical moieties resulting from bonding. In specific embodiments, the spacer of the linker moiety is an alkylene chain having 1-12, 2-6 or 2-6 carbon atoms which bridges the chemical moieties resulting from bonding and in which one or more —$CH_2$— groups are replaced with —O—, —S—, —NH—, —CO—, a double bond, a triple bond, —CO—O—, —CO—NH—, —CO—S—, —O—CO—, —S—CO—, or —NH—CO—. In specific embodiments, the spacer of the linker moiety is an alkylene chain having 1-12, 2-6 or 2-6 carbon atoms which bridges the chemical moieties resulting from bonding and in which one —$CH_2$— group is replaced with —O—, —S—, —NH—, —CO—, a double bond, a triple bond, —CO—O—, —CO—NH—, —CO—S—, —O—CO—, —S—CO—, or —NH—CO—. In specific embodiments, the spacer of the linker moiety is an alkylene chain having 1-12, 2-6 or 2-6 carbon atoms which bridges the chemical moieties resulting from bonding and in which one, two or three —$CH_2$— groups are replaced with —O—, or —S—. In specific embodiments, the spacer of the linker moiety is an alkylene chain having 1-12, 2-6 or 2-6 carbon atoms which bridges the chemical moieties resulting from bonding and in which one or two —$CH_2$— groups are replaced with a double bond. Spacers can include among others —$(CH_2$—$CH_2$—$O)_p$—, where p is 1-6, 2-6, or 2-4.

It will also be appreciated that the linker can derive in full or in part from an art-recognized crosslinking reagent, such as a homo- or heterobifunctional crosslinking reagent.

In a specific embodiment, the invention provides pharmaceutical compositions useful for treatment of cancer and more particularly for use for regression of tumors which comprise a therapeutically effective amount of L-rhamnose-antigen lipid conjugates alone or in combination with one or more antibodies, and/or one or more antigen lipid conjugates, where the antigen is other than L-rhamnose antigen, and/or one or more lipids (not carrying L-rhamnose antigen) which can facilitate insertion of antigen-lipid conjugates into cell membranes. Pharmaceutical composition can also comprise a pharmaceutically acceptable carrier.

In specific embodiments, the antibodies of the compositions are antibodies which inhibit or prevent the functioning of complement inhibitory factors which can be expressed in cancer cells or tissue, for example, protein DAF (CD55), CD59 (protectin), CD46 (membrane co-factor), or CR1 [Gelderman et al. (2004) Trends Immunology 25:158-164; Fletcher, A., et al., Immunology, 1992. 75(3): p. 507-12; Bryant, J. A., A. Fletcher, and F. F. Yuan, 1993. 9(3): p. 68-73. Liu et al. JEM 2005(4):567; Niehaus et al. Am J. Pathology 1996 149(1) July 1996:129.] These references are incorporated by reference herein for their description of useful antibodies. In specific embodiments, the antibodies can otherwise affect the regulation of the immune system. For example, Cytotoxic T-Lymphocyte-4 receptor (CTLA-4, also called CD152) downregulates the immune system. Antibodies which block the CTLA-4 receptor, such as ipilimumab, can also be employed in the pharmaceutical compositions of this invention.

The compositions of the invention can further include other immunomodulatory agents as are known in the art. For example useful immunomodulatory agents include among others interferon-gamma or interleukin-2. Pharmaceutical compositions of this invention can be co-administered if desired with other immunomodulatory agents.

In specific embodiments, non-L-rhamnose antigen-lipid conjugates are hapten-lipid conjugates. Hapten-lipid conjugates include among others those in which the hapten is nitrophenyl, 2,4-dinitrophenol or trinitrophenyl) (NP, DNP or TNP), or fluorescein or α-Gal. Non-L-rhamnose antigens antigens include those present in the normal CDC (Centers for Disease Control and Prevention) vaccination schedule. These include polysaccharide which are found in the *haemophilus influenzae* b (Hib) vaccine, and those in the meningococcal vaccine (Men. groups A, C, Y. and W-135 types, as well as a diptheria oigosaccharide). Non-L-rhamnose antigens antigens also include protein antigens used in vaccination such as tetanus toxoid, diptheria toxoid, and other proteinaceous components. Art-known immunodominant peptide fragments can also be used.

Pharmaceutical compositions as described herein are useful in the methods described herein.

It will be appreciate that antibodies as discussed above can be administered separately from the pharmaceutical compositions of this invention. Additionally, the pharmaceutical compositions of this invention can be combined with other chemotherapeutics. Chemotherapeutic agents which affect the regulation of the immune system are of particular interest. In a specific embodiment, pharmaceutical compositions of this invention can be used in combination with the chemotherapeutic agent fludarabine which downregulates CD55. [DiGaetano et al., J. Haematol. (September 2001) 114(4):800-809]

A pharmaceutical composition or medicament of the invention can be prepared by admixture of one or more L-rhamnose antigen-lipid conjugates with an appropriate carrier. In a specific embodiment, the carrier comprises lipids other than the L-rhamnose antigen-lipid conjugates. The pharmaceutical composition may contain a diluent, binder, filler, disintegrant, coloring agent, lubricant or preservative such as are known in the art.

A pharmaceutical composition of the invention can be in unit dosage form and in a form adapted for use in the medical or veterinarial fields. For example, such preparations may be in a pack form accompanied by written or printed instructions for use as an agent in the treatment of the conditions noted herein. As is understood in the art, the suitable dosage range for the lipid conjugates of the invention depends on the specific compound to be employed and on the condition of the individual being treated.

The compounds of this invention may be formulated in an injectable form in an aqueous or non-aqueous solution, suspension or emulsion in a pharmaceutically acceptable liquid, e.g. sterile pyrogen-free water or an acceptable lipid or oil or a mixture of such materials.

The invention provides methods for introducing L-rhamnose lipids into cell membranes such that L-rhamnose antigens are displayed on the cell surface. In specific embodiments, the cells are tumor cells. In specific embodiments, the cells are melanoma cells. In this method, cells are contacted with one or more L-rhamnose antigen-lipid conjugates of this invention such that L-rhamnose antigen-lipid conjugates are inserted into the cell membrane. Insertion of the L-rhamnose antigen-lipid conjugates into cell membranes results in immune-mediated detection of the cells, and targeting of the cells for lysis and destruction.

The invention provides methods for killing cells or otherwise inhibiting cell growth in a biological system which comprises anti-L-rhamnose antibodies which comprises, introducing L-rhamnose lipid conjugates into the cell membranes such that the cells are thereby targeted by the anti-L-rhamnose antibodies. Targeted cells are killed or their growth is inhibited.

In a specific embodiment, tumor cells or tumor tissue are contacted with an effective amount of L-rhamnose antigen-lipid conjugates such that L-rhamnose antigen-lipid conjugates are inserted into tumor cells, particularly cancer cells, to target the cells and tissue for immune response that results in lysis or killing of cells or tissue and regression of tumors. In a specific embodiment, contact of tumor cells and tissue with L-rhamnose antigen-lipid conjugates can destroy micrometastases beneficial to inhibiting metastasis. In a specific embodiment, the L-rhamnose antigen-lipid conjugates are contacted with tumor cells or tissue by intratumoral injection of a pharmaceutically acceptable composition containing one or more L-rhamnose antigen-lipid conjugates. In another specific embodiment, the L-rhamnose antigen-lipid conjugates are contacted with tumor cells or tissue by application of a pharmaceutically acceptable composition directly to the tumor cells or tissue, for example by application of a solution, suspension, ointment, or lotion containing an effective amount of one or more L-rhamnose antigen-lipid conjugates. In a specific embodiment, the pharmaceutical composition is applied topically to tumor cells or tissue. In a specific embodiment, the one or more L-rhamnose antigen-lipid conjugates are in the form of one or more lipid aggregates, which can include bilayers, micelles, vesicles, liposomes or mixtures thereof.

In a specific embodiment, contacting tumor cells or tissue with L-rhamnose-antigen lipid conjugates results in the display of L-rhamnose antigen on the cells which results in inflammation which can destroy the tumor or tumor tissue. This treatment can convert the tumor cells and tissue into an in situ autologous tumor vaccine.

BRIEF DESCRIPTION OF THE DRAWINGS

FIG. 1 also includes a Table of average corrected RU for antibodies to each antigen. Antibodies recognizing rhamnose are of higher titer than those recognizing αGal.

FIG. 3 also includes a Table showing percentage loss calculated as (RUT2)/RuT1. All RU were corrected by reference subtraction. Rhamnose-labeled flow cells retained antibody longer than αGal and DNP flow cells in most cases indicating that the rhamnose-anti-rhamnose complexes are the more stable.

DETAILED DESCRIPTION OF THE INVENTION

Figure 1:
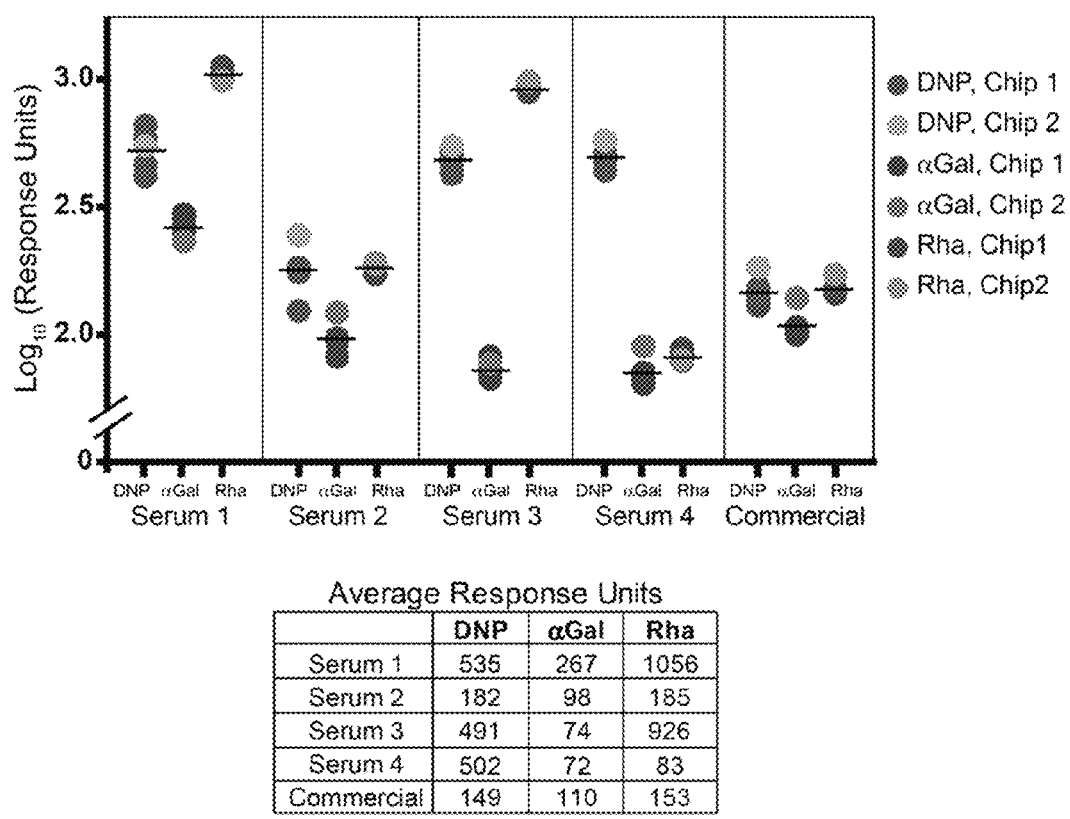
FIG. 1 illustrates a graph of corrected response units ($RU_{antigen}$-$RU_{reference}$) of antibodies obtained from serum samples bound to the antigens DNP, αGal and Rha.

This invention provides L-rhamnose antigen lipid conjugates which can be inserted into cell membranes and which are capable of recruiting endogenous anti-Rha antibodies to the cell surface initiating cytotoxic pathways including complement. The lipid portion of the conjugate partitions into cell membranes and so can be used as a labeling agent to label the cell surface with L-rhamnose antigen. The lipid conjugates and methods of the invention are particularly useful for the recruitment of the immune system to sites of tumor growth (in humans or non-human animals) for the purpose of initiating an anti-tumor antigen response. This method is a promising approach to cancer treatment. L-rhamnose antigens are widely-recognized foreign antigens, allowing endogenous serum anti-rhamnose antibodies to bind and initiate immune responses leading to both tumor clearance and immune system priming.

In an embodiment, lipids bearing L-rhamnose antigen-modified headgroups can successfully deliver antigen to the cell surface and mark the cell for destruction by the immune system. In a specific embodiment, cells are contacted with L-rhamnose antigen-lipid conjugates to label the cells with L-rhamnose antigen which induces complement-mediated cell death. In specific embodiments, the cells are tumor cells, particularly human tumor cells. In a specific embodiment the cells are melanoma cells. Contacting of cells with L-rhamnose antigen-lipid conjugates can occur in vitro, in vivo or ex vivo. Contacting includes local application of pharmaceutically acceptable compositions of this invention comprising one or more L-rhamnose antigen-lipid conjugates. Such compositions can further comprise one or more antigen-lipid conjugates other than L-rhamnose antigen-lipid conjugates, e.g., hapten-lipid conjugates, such as DNP-lipid conjugates), one or more antibodies to complement inhibitory factors and/or one or more lipids (with no antigen conjugated thereto).

In a specific embodiment, that labeling cells with L-rhamnose antigen will initiate cell-dependent cytotoxic pathways in vivo which will serve to create a robust cytotoxic T cell response and transfer cell labeled with L-rhamnose antigens to draining lymph nodes, further amplifying the anti-tumor response.

The L-rhamnose antigen-lipid conjugates of this invention provide significant benefit over the use of αGal-ceramide conjugates. L-rhamnose antigens, the recruiting antigen which recognizes L-rhamnose, are typically more abundant than those recognizing αGal. The L-rhamnose antigen-lipid conjugates of this invention include synthetically prepared conjugates which are well-defined, well-characterized and free of contamination from deleterious animal products in contrast to materials that are isolated and animal-derived (e.g., from rabbit erythrocytes). Modular methods for antigen-lipid conjugate synthesis are provided which allow for rapid interchange of both antigen and lipid portions to quickly assess a variety of lipids and antigens. Additionally, L-rhamnose and related L-rhamnose antigens are commercially available (or readily made by known methods) and are significantly easier to manipulate compared to αGal, making the use of L-rhamnose-antigen lipid conjugates more cost-effective and efficient than αGal-lipid conjugates.

L-Rhamnose Antigen-Lipid Conjugate

In a specific embodiment, the L-rhamnose antigen-lipid conjugate has a structure as illustrated in which one or more L-rhamnose antigens are conjugated by a linker to a lipid:

(L-Rha)$_n$-LK-lipid

L-Rha is an L-rhamnose antigen which can be an L-rhamnose monosaccharide (an L-rhamnose moiety) or a dimer or oligomer of L-rhamnose monomers. LK is a divalent or multivalent linker and the lipid is a lipid that can be inserted into a cell membrane (animal, particularly human). The conjugate contains at least two L-rhamnose moieties, so that when the antigen is an L-rhamnose n is 2 or more and when the antigen is a dimer or oligomer n is 1 or more. The number of L-rhamnose antigens or moieties in the antigen-lipid complex is such that insertion of the antigen-lipid conjugate is not disrupted or inhibited. In a specific embodiment, the L-rhamnose antibody is an L-rhamnose and n is 2 or more, 2-500, 2-256, or 2-100. In a specific embodiment, the L-rhamnose antibody is a dimer or oligomer and n is 1-10, n is 1-5 or n is 2-5.

L-rhamnose antigen-lipid complexes carrying a single L-rhamnose moiety have been found not to provide sufficient effect to cause significant cell lysis and/or cell killing.

L-Rhamnose Antigen

The lipid conjugates of this invention comprise 2 or more L-rhamnose moieties. In one embodiment, the L-rhamnose moieties are two or more L-rhamnose monosaccharides which are conjugated to the lipid by a multivalent linker. In specific embodiments, 2, 4, 8, 16 or 32 L-rhamnose monosaccharides are conjugated to the lipid by a multivalent linker. In another embodiment, one or more L-rhamnose dimers or L-rhamnose oligomers having 3-25, 3-10 or 3-6 L-rhamnose monomers is conjugated to the lipid by a linker which can be a multivalent linker. In specific embodiments, the dimer or oligomer comprises alpha-1,3-linked L-rhamnose residues. In specific embodiments, the L-rhamnose oligomer consists only of L-rhamnose residues.

L-rhamnose dimers and oligomers are commercially available or can be prepared by known methods from known starting materials. For example, L-rhamnose dimers and oligomers can be prepared as described in EP patent application EP 612527 from rhamnan.

Linker

In the lipid conjugates of this invention, lipids are typically linked to the two or more L-rhamnose moieties, or L-rhamnose oligomers by a linker. The linker comprises chemical moieties that result from the conjugation method employed and also optionally can provide for selected spacing between the lipid and the L-rhamnose moiety or L-rhamnose oligomer. A wide variety of linker moieties can be employed as will be appreciated by one of ordinary skill in the art.

In specific embodiments, a multivalent linker can be employed which provides for conjugation to the lipid and two or more L-rhamnose monosaccharides, two or more L-rhamnose dimers or two or more L-rhamnose oligomers.

In specific embodiments, a divalent linker can be employed which provides for conjugation of the lipid to an L-rhamnose dimer or oligomer. Divalent linkers include, among others, those of structure:

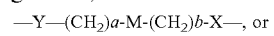

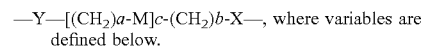

In specific embodiments, a multivalent linker can be employed which provides for conjugation to the lipid and two or more L-rhamnose monosaccharides, two or more L-rhamnose dimers or two or more L-rhamnose oligomers. Multivalent linkers include among others those of structure:

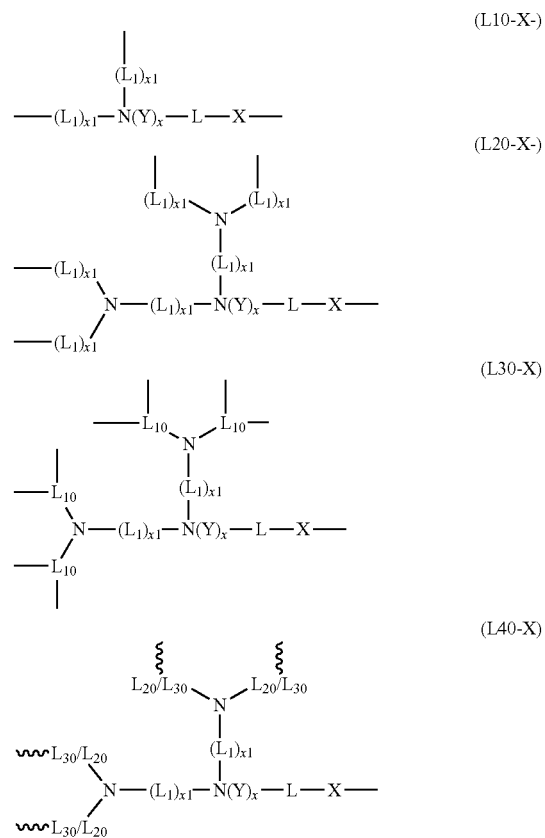

where L1 is —(Y)y-(CH$_2$)a-M-(CH$_2$)b-(X)x-, or —(Y)y-[(CH$_2$)a-M]c-(CH$_2$)b-(X)x-;

x, x1, and y are 0 or 1 to show absence or presence of X or Y;

X and Y are the same or different and are selected from —CO—, —O—CO—, —CO—O—, —NHCO—, —CONH—, —SCO—, —CO—S—, S—CS—, —SC—S—, —NH—SO$_2$—, —SO$_2$—NH—, —O—, —NH$_2$—, —NH—CO—O—, —NH—CO—NH—, —O—CO—O—, or —S—CO—O—;

M is absent or present and is selected from an arylene, heteroarylene, cycloalkylene, (e.g., a 1,4-phenylene, or a 1,4-cyclohexylene), a cis or trans-double bond, —O—, —S—, —S—S—, —CO—, —O—CO—, —CO—O—, —NH—CO—, —CO—NH—, —NH—SO$_2$—, —SO$_2$—NH—, —NH$_2$—, —N(R')$_2$—, —NH—CO—NH—, —S—CO—, —O—CS—, —S—CS—, —SC—S—, or —O—CO—O—;

a and b are zero or integers that range from 1-30, where at least one of a or b is non-zero and where a+b is 1-50, 1-20, 1-12, 1-6, 2-12, 2-10 or 2-8 or 2-6;

c is an integer ranging from 1-12, 1-6, or 1-3; and wherein one or more —CH$_2$— groups in the linker are substituted with one or two —OH groups, wherein one or more —CH$_2$— are replaced with —O—, —S— or —NH—, and/or wherein one or more —CH$_2$—CH$_2$— groups are replaced with —CH═CH— (which may be cis or tans). Multivalent linkers of this invention can be dendrons or dendrimers as these terms are broadly used in the art.

In specific embodiments, X and Y are independently —O—, —NH—, O—CO—, —CO—O—, —NH—CO—, or —CO—NH—. In specific embodiments, M is absent. In specific embodiments, (a+b) is 2-8 or 4-6.

Lipids

The invention provides rhamnose antigen-lipid conjugates particularly for insertion into cell membranes to target anti-Rha antibody to the cells carrying rhamnose antigen-lipid conjugates. The lipid conjugates and methods of the invention can employ any lipid which will insert into a cell membrane, particularly an animal cell membrane and more particularly a human cell membrane. Of particular interest is insertion of rhamnose-lipid conjugates into tumor cell membranes.

In a specific embodiment, for ease of handling lipids useful in the invention have a transition or melting temperature below room temperature.

Lipids useful in the conjugates and methods of this invention include among others fatty acids (saturated, unsaturated or polyunsaturated), glycerolipids, e.g., mono-, di- or tri-substituted glycerols, mono-, di- or triacyl glycerols, mono-, di- or trialkylglycerols; glycerophospholipids, e.g., glycerophosphoethanolamines, glycerophosphoserines, glycerophosphoglycerols; sphingolipids, e.g., sphingosines, ceramides, dihydroceramides, phytoceramines (N-acyl-4-hydroxysphinganines), ceramide phosphoethanolamines; sterols (e.g., cholesterol, stigmasterol, ergosterols and derivatives thereof); or steroids (e.g., estrogens, particularly those with a 3-OH group, e.g., estradiol, estrone). In specific embodiments, the lipids are glycerophosphoethanolamines, including among others, diacylglycerophosphoethanolamines, 1-alkyl, 2-acylglycerophosphoethanolamines, 1-acyl, 2-alkylglycerophosphoethanolamines, 1Z-alkenyl, 2-acylglycerophosphoethanolamines, dialkylglycerophosphoethanolamines, monoacylglycerophosphoethanolamines, monoalkylglycerophosphoethanolamines, or 1Z-alkenylglycerophosphoethanolamines. In other specific embodiments the lipids are sphingolipids, or ceramides. In other specific embodiments, the lipid is phosphatidylinositol. In other specific embodiments the lipids are sterols, particularly cholesterol and hydroxyl-substituted, oxo-substituted or dehydro derivatives thereof. In other specific embodiments, the lipids are estrogens.

In specific embodiments, the lipid is a lipid of formula PEX, PEX1, PEAX, PEAX1, CerX or CerX1:

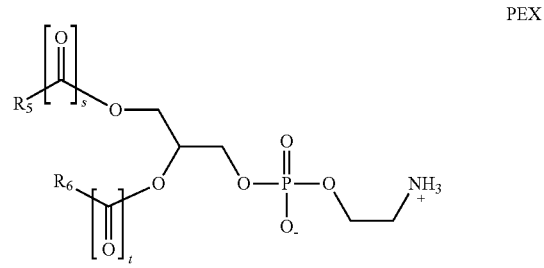

PEX

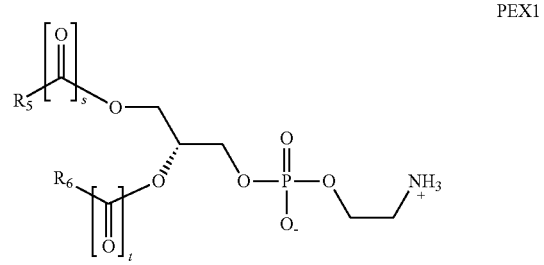

PEX1

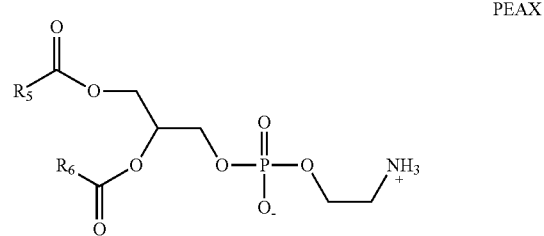

PEAX

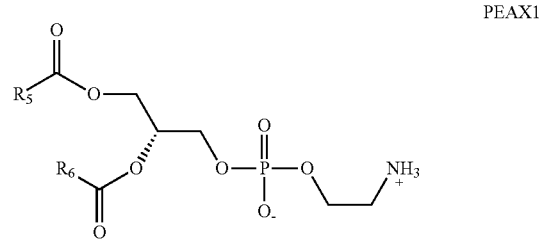

PEAX1

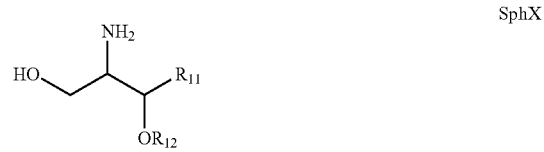

SphX

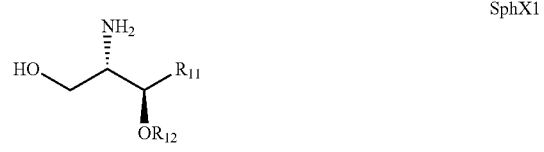

SphX1

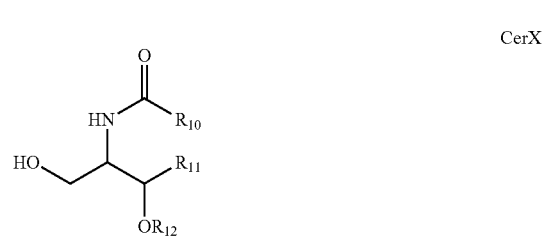

CerX

13
-continued

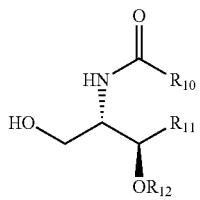

CerX1

14
-continued

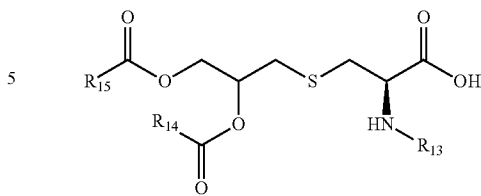

PAMCYC-II where:
s and t are independently 0 or 1 to indicate the presence or absence of the —CO—, both of s and t can be 0, both s and t can be 1, and one of s or t can be 0, and the other of s or t can be 1;
$R_5$ and $R_6$ are independently selected from alkyl or alkenyl groups having 7-32 carbon atoms which are optionally substituted with 1-6 hydroxyl groups;
$R_{10}$ and $R_{11}$ are independently selected from alkyl or alkenyl groups having 7-32 carbon atoms which are optionally substituted with 1-6 hydroxyl groups; and
$R_{12}$ is H or a protecting group, such as an acyl group (having 1-10, 1-6 or 1-3 carbon atoms), and more specifically is an acetyl group;

In specific embodiments, $R_5$ and $R_6$ have 10-20 carbon atoms. In specific embodiments, $R_5$ and $R_6$ have 12-18 carbon atoms. In specific embodiments, one or both of $R_5$ and $R_6$ are monounsaturated. In specific embodiments, one or both of $R_5$ and $R_6$ are polyunsaturated having 2-4 double bonds.

In specific embodiments, $R_{10}$ and $R_{11}$ have 10-20 carbon atoms. In specific embodiments, $R_{10}$ and $R_{11}$ have 12-18 carbon atoms. In specific embodiments, one or both of $R_{10}$ and $R_{11}$ are monounsaturated. In specific embodiments, one or both of $R_{10}$ and $R_{11}$ are polyunsaturated having 2-4 double bonds.

In specific embodiments one or more of $R_5$, $R_6$, $R_{10}$ or $R_{11}$ is selected from:
Straight-chain alkyl having 7-32 or 10-20 carbon atoms;
—$(CH_2)_c$—CH=CH—$(CH_2)_d$—$CH_3$, where the double bond is cis or trans, preferably cis, where c and d are integers ranging from 1 to 29 and c+d is 10-29;
—$(CH_2)_c$—CH=CH—CH=CH—$(CH_2)_d$—$CH_3$, where the two double bonds are independently in the E or Z configuration, where c and d are integers ranging from 1-27 and c+d is 10=27;
—$(CH_2)_c$—CH=CH—$CH_2$—CH=CH—$(CH_2)_d$—$CH_3$, where the two double bonds are independently in the E or Z configuration, where c and d are integers ranging from 1-26 and c+d is 10=26;
—CH=CH—$(CH_2)_c$—$CH_3$, where c is an integer from 7-29, in a specific embodiment c is 12; or
—CH=CH—CH=CH—$(CH_2)_c$—$CH_3$, where c is an integer from 6-29, in a specific embodiment c is 6.

In specific embodiments the lipid is a Pam-Cys-OH, a $Pam_2$-Cys-OH, a $Pam_3$-Cys-OH or a related lipid of formula PAMCYS-I or PAMCYS-2:

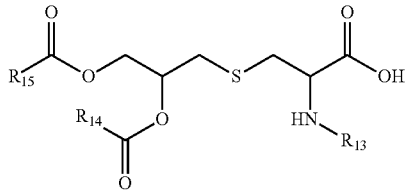

PAMCYS-I where:
$R_{13}$ is independently hydrogen, or —CO—$R_{16}$, where $R_{16}$ is selected from hydrogen or alkyl or alkenyl groups having 7-32 carbon atoms which are optionally substituted with 1-6 hydroxyl groups; and
$R_{14}$-$R_{15}$ are independently selected from hydrogen or alkyl or alkenyl groups having 7-32 carbon atoms which are optionally substituted with 1-6 hydroxyl groups; and wherein at least one of $R_{14}$-$R_{15}$ is a group other than a hydrogen. In specific embodiments, $R_{13}$-$R_{15}$ are alkyl groups having 13 to 17 carbon atoms and more specifically having 15 carbon atoms. In specific embodiments, both $R_{14}$ and $R_{13}$ are H. In specific embodiments, $R_{14}$ is H. In specific embodiments, both $R_{13}$ and $R_{15}$ are H. In specific embodiments $R_{13}$ is H. In specific embodiments, $R_{15}$ and $R_{16}$ are the same alkyl group. In specific embodiments, $R_{15}$ and $R_{14}$ are the same alkyl group. In specific embodiments, $R_{14}$, $R_{15}$ and $R_{16}$ are the same alkyl group. In specific embodiments, the lipid is PAM1-Cys, PAM2-CYs or PAM3-Cys. It is noted that PAM2-Cys and PAM3-CYs are TLR2 agonists that would be expected to further boost immune response. [Buskas, T., Ingale, S, and Boons, G.-J. (2005), Towards a Fully Synthetic Carbohydrate-Based Anticancer Vaccine Synthesis and Immunological Evaluation of a Lipidated lycopeptide Containing the Tumor-Associated Tn Antigen. Angew. Chem. Int. Ed., 44: 5985-5988]

In a specific embodiment, the lipid is a TLR2 agonist, such as monophosphoryl Lipid A [Mata-Haro, V. et al. (2007) Science 316(5831) 1628-1632; Wang, Q. et al. (2012) ACS Chem. Biol. 7(1) 235-240] or lipoaminoacids [Abu-Baker, M. et al. (2012) J. Medicinal Chem. 55(15): 6968-6974], such as $PAM_2CS$(S—[2,3-bis(palmitoyloxy)-(2RS)-propyl]-R-cysteinyl-S-serine) and TLR2 agonist analogues thereof. [See: Wu, W. et al. J. MED. Chem. 2010, 53:3198-3213; G. Agnihotri et al. (December 2011) J. Med. Chem. 54(23):8148-8160]. The foregoing references are incorporated by reference herein in their entirety for descriptions of lipids which are TLR2 agonists.

In specific embodiments, the lipid is a lipid of formula:

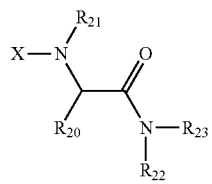

where X is —CO—, —O—CO— or $H_2NCO$— or is not present;
$R_{21}$ is hydrogen or an alkyl group;
$R_{22}$ and $R_{23}$ are independently hydrogen, or —CO—$R_{16}$, where $R_{24}$ is selected from hydrogen or alkyl having 1-6 carbon atoms which are optionally substituted with 1-6 hydroxyl groups; and $R_{20}$ is an alkyl or alkenyl group having 7-32 carbon atoms which are optionally substituted with 1-6 hydroxyl groups. In specific embodiments, $R_{20}$ is an alkyl group having 9-21 carbon atoms and more specifically having 15-17 carbon atoms. In specific embodiments, both all of $R_{21}$-$R_{23}$ are hydrogens.

In specific embodiments, lipids are bonded to the $(L-Rha)_n$ moiety by a divalent linker.

In specific embodiments, lipids are bonded to the $(L-Rha)_n$ moiety by a multivalent linker.

In a specific embodiment, the lipid conjugate employs a divalent linker and is a specific lipoamino acid or variant thereof of formula:

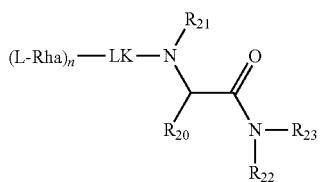

where $R_{21}$ is hydrogen or an alkyl group;
$R_{22}$ and $R_{23}$ are independently hydrogen, or —CO—$R_{16}$, where $R_{24}$ is selected from hydrogen or alkyl having 1-6 carbon atoms which are optionally substituted with 1-6 hydroxyl groups; and
$R_{20}$ is an alkyl or alkenyl group having 7-32 carbon atoms which are optionally substituted with 1-6 hydroxyl groups. In specific embodiments, $R_{20}$ is an alkyl group having 9-21 carbon atoms and more specifically having 15-17 carbon atoms. In specific embodiments, both all of $R_{21}$-$R_{23}$ are hydrogens.

In a specific embodiment, the lipid conjugate employs a multivalent linker -$(LK)_m$ and is a specific lipoamino acid or variant thereof of formula:

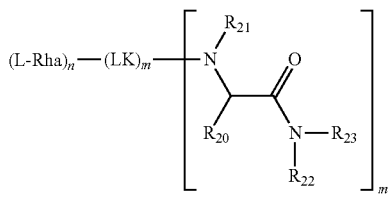

where:
m is 2-4;
$R_{21}$ is hydrogen or an alkyl group;
$R_{22}$ and $R_{23}$ are independently hydrogen, or —CO—$R_{16}$, where $R_{24}$ is selected from hydrogen or alkyl having 1-6 carbon atoms which are optionally substituted with 1-6 hydroxyl groups; and
$R_{20}$ is an alkyl or alkenyl group having 7-32 carbon atoms which are optionally substituted with 1-6 hydroxyl groups.

In specific embodiments, $R_{20}$ is an alkyl group having 9-21 carbon atoms and more specifically having 15-17 carbon atoms. In specific embodiments, both all of $R_{21}$-$R_{23}$ are hydrogens. In specific embodiments, m is 2.

In specific embodiments, the rhamnose moiety is not a rhamnose dimer or rhamnose oligomer.

The term alkyl refers to a saturated hydrocarbon monovalent radical. In the present application alkyl groups are preferably straight-chain and not branched. However, branched alkyl groups where the branch is formed with a methyl group are useful in the invention. Alkyl groups can be substituted with one or more hydroxyl groups or one or more methyl groups. Alkyl groups can have 1-32 carbon atoms. Alkyl groups for hydrophobic lipid tails preferably have 8-32, 10-22, 10-20, 10-18, 12-18, or 12-15 carbon atoms. The term alkylene refers to a divalent saturated hydrocarbon moiety —$(CH_2)_x$—, where x is the number of carbon atoms.

The term alkenyl refers to a mono- or polyunsaturated hydrocarbon monovalent radical, having one or more double bonds. In the present application alkenyl groups are preferably straight-chain and not branched. However, branched alkenyl groups where the branch is formed with a methyl group are useful in the invention. Alkenyl groups can be substituted with one or more hydroxyl groups or one or more methyl groups. Alkenyl groups can have 1-32 carbon atoms. Alkenyl groups for hydrophobic lipid tails preferably have 8-32, 10-22, 10-20, 10-18, 12-18, or 12-15 carbon atoms.

Acyl groups refer to —CO—R groups where R is an alkyl group or an alkenyl group as defined above. Acyl groups also include those where R is a C1-C3 alkyl group, which can be employed as protecting groups.

In specific embodiments, the L-Rha antigen-lipid conjugates comprising at least two L-rhamnose moieties, of the invention can be employed to convert tumor lesions into autologous vaccine by intratumoral injections of the L-Rha antigen-lipid conjugates as is described in Galili et al. Cancers 2010 2(2), 773-793 for application of α-Gal antigens. This reference is incorporated by reference herein in its entirety for descriptions of this method. This method is particularly applicable to treatment of melanoma.

In specific embodiments, the L-Rha antigen-lipid conjugates comprising at least two L-rhamnose moieties, of the invention can be employed to prepare autologous vaccine by modification of cancer cells to display L-Rha antigens as is described in Berd, D. Vaccine 2001 19(17-19):2565-70. This reference is incorporated by reference herein in its entirety for descriptions of this method. This method is particularly applicable to treatment of melanoma and more particularly to the treatment of metastatic melanoma.

The invention comprises pharmaceutically acceptable compositions comprising one or more L-rhamnose antigen-conjugates of this invention in combination with a pharmaceutically acceptable carrier. These compositions can contain lipids, antigen conjugates and/or antibodies as noted elsewhere herein. The composition of this invention containing lipid conjugates and optionally containing lipids can be processed by various art known lipid preparation methods, such as extrusion, sonication, or the like to form more uniform lipid structures, including liposomes, without detrimental effects on cell membrane insertion.

The invention provides methods for treatment of cancer. More specifically, the invention provides methods for administering L-rhamnose antigen-lipid conjugates to tumor cells or tumor tissue to mediate immune responses that result in tumor cell lysis and/or killing and/or tumor regression. In a specific embodiment, lipid conjugates of this invention or pharmaceutical compositions comprising a therapeutically effective amount of one or more of such lipid conjugates are employed. In other embodiments, pharmaceutical composition of this invention comprise one or more L-rhamnose antigen-lipid conjugates, one or more antigen-lipid conjugates that are not L-rhamnose antigen-lipid conjugates, and/or one or more antibodies to complement inhibitory factors and/or one or more lipids (with no antigen conjugated thereto). Lipids combined in the pharmaceutical compositions herein can be selected from any of the lipids that are described herein above for use in making lipid conjugates of the invention.

The treatment methods of the invention are applicable to treatment of individuals having endogenous anti-rhamnose antibodies who are in need of such treatment, for example, who have, or are diagnosed as having, a tumor, tumor tissue or tumor lesion. In this method, cancer or tumor cells are contacted with a pharmaceutical composition of the invention. Contact can be by administration of the pharmaceutical composition to the tumor cell, tumor tissue, tumor or tumor lesion by any method such that antigen-lipid conjugates of the invention are displayed on tumor cells. Administration can be by intratumoral injection, for example, a skin lesion intradermal injection can be applied. Administration can be image guided injection, by endoscopy, bronchoscopy, cystoscopy, colonoscopy, laparoscopy, and catheterization. Any form of administration that facilitates contact of tumor cell, tumor tissue or tumors with a pharmaceutical composition of this invention can be employed. Administration can be employed during surgery for resection or removal tumor tissue. In specific embodiments, the tumor or tumor tissue originates or is located in the peritoneum, liver, pancreas, lung, urinary bladder, prostate, uterus, cervix, vagina, breast, skin, brain, lymph node, head and neck, stomach, intestine, colon, or ovaries. The source or location of the tumor is not critical, however, methods herein are particularly useful for tumors or lesions that can be accessed by intradermal injection. The methods of the invention are particularly useful for treatment of surface tumors or lesions.

In an embodiment, administration of pharmaceutical compositions of this invention converts a treated solid tumor, tumor tissue or a tumor or cancer cell into an autologous vaccine. In an embodiment, administration of pharmaceutical compositions of this invention induces an antigen presenting cell to produce an autologous vaccine against a solid tumor, tumor tissue or tumor or cancer cell. In a specific embodiment, administration is to a primary tumor or primary tumor tissue. In another embodiment, administration is to a metastatic tumor or metastatic tissue. In a specific embodiment, administration of a pharmaceutical composition of the invention slows or stops the growth of a tumor or tumor tissue. In a specific embodiment, administration of a pharmaceutical composition of the invention causes reduction in size of a tumor. In a specific embodiment, administration of a pharmaceutical composition of the invention causes destruction of a tumor or tumor tissue.

L-Rhamnose-lipid conjugates, lipids, antigens and other components of compositions of this invention may be in the form of salts.

The invention further provides therapeutic compositions comprising a therapeutically effective amount of one or more L-rhamnose antigen-lipid conjugates of this invention in combination with a suitable pharmaceutically acceptable carrier. Additional optional components of therapeutic compositions include, among others, antigens particularly those as described herein, antigen-lipid conjugates other than L-rhamnose antigen-lipid conjugates, and lipids which can facilitate introduction of L-rhamnose antigen-lipid conjugates into cell membranes. Therapeutic compositions include those useful for application to tumors, tumor tissue or lesions. In a specific embodiment, therapeutic compositions include those suitable for topical application to tissue. In a specific embodiment, therapeutic compositions include those suitable for topical application to skin.

The invention additionally provides one or more L-rhamnose antigen-lipid conjugates for use in the treatment of cancer. More specifically, the invention provides one or more L-rhamnose antigen-lipid conjugates for use in removing tumors or tumor tissue or for use in decreasing the size of tumors or tumor tissue. Further, the invention provides one or more L-rhamnose antigen-lipid conjugates for use in the manufacture of a medicament for treating cancer, or for removing or decreasing the size of tumors or tumor tissue.

The methods of the invention can be combined with specific vaccination to generate endogenous anti-rhamnose antibodies or to encourage selectively higher formation of anti-rhamnose IgG or anti-rhamnose IgM. In a specific embodiment, the methods of the present invention can be combined with the use of the pneumococcal conjugate vaccine, Prevnar 13 (Pfizer) [Gruber, W. C., et al. Development and clinical evaluation of Prevnar 13, a 13-valent pneumococcal CRM(197) conjugate vaccine. Annals of the New York Academy of Sciences, 2012. 1263: p. 15-26]. This vaccine is likely to generate the requisite antibodies [Bentley, S. D., et al., Genetic Analysis of the Capsular Biosynthetic Locus from All 90 Pneumococcal Serotypes. PLoS Genetics, 2006. 2(3): p. e31; Pazur, J. H., et al. Anti-Rhamnose Antibodies Having Specificity for Rhamnose-Containing, Streptococcal Heteroglycans. Carbohydrate Research, 1983. 124: p. 253-263.].

The methods of the invention can also be combined with the use of the cytotoxic T lymphocyte antigen 4 (CTLA4) blocking antibody, ipilimumab. Treatment with this antibody un-inhibits cytotoxic T cells and lowers their threshold for response. Its use in conjunction with the methods of the present invention can enhance the desired cellular response.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. A number of specific groups of variable definitions have been described herein. It is intended that all combinations and subcombinations of the specific groups of variable definitions are individually included in this disclosure. Compounds described herein may exist in one or more isomeric forms, e.g., structural or optical isomers. When a compound is described herein such that a particular isomer, enantiomer or diastereomer of the compound is not specified, for example, in a formula or in a chemical name, that description is intended to include each isomers and enantiomer (e.g., cis/trans isomers, R/S enantiomers) of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Isotopic variants, including those carrying radioisotopes, may also be useful in diagnostic assays and in therapeutics. Methods for making such isotopic variants are known in the art. Specific names of compounds are intended to be exemplary, as it is known that one of ordinary skill in the art can name the same compounds differently.

Molecules disclosed herein may contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. Salts include acidic and/or basic salts formed with inorganic and/or organic acids and bases. In addition, if a molecule of the invention contains both a basic moiety and an acidic moiety, zwitterions ("inner salts") may be formed and are also considered salts. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt. In embodiments, herein salts are pharmaceutically acceptable salts.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Molecules and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention.

Every formulation or combination of components described or exemplified herein can be used to practice the invention, unless otherwise stated.

The use of "a" means "one" or "one or more."

One of ordinary skill in the art will appreciate that methods, procedures and materials, such as starting materials, reagents, reaction methods, purification methods, biological assays, other than those specifically exemplified herein can be employed in the practice of the invention without resort to undue experimentation. All art-known functional equivalents, of any such methods, materials and conditions are intended to be included in this invention.

Whenever a range is given in the specification, for example, a range of numbers, a range of any integer, a temperature range, a time range, or a composition range, all intermediate ranges and subranges, as well as all individual values included in the ranges given are intended to be included in the disclosure.

This description may include statements regarding the mechanism by which the L-Rha antigen-lipid conjugates function. Such statements represent the inventors' current understanding of the subject matter herein and are not intended to limit the invention.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the broad term "comprising", particularly in a description of components of a composition, the recitation of steps in a method or in a description of elements of a device, is intended to encompass and describe the terms "consisting essentially of" or "consisting of".

Although the description herein contains many specific recitations, these should not be construed as limiting the scope of the invention, but as merely providing illustrations of some of the embodiments of the invention. Each references cited herein is hereby incorporated by reference herein in its entirety. In the case of any inconsistency between the content of a cited reference and the disclosure herein, the disclosure of this specification is to be given priority. Some references cited herein are incorporated by reference herein to provide details of conjugation reactions useful in the invention, starting materials and reagents useful in the invention, examples of linker structures and lipids that are useful in the invention, sources of starting materials, assay conditions, particularly, additional methods of analysis and additional uses of the lipid-conjugates of the invention.

THE EXAMPLES

Example 1: Rhamnose-Lipid Conjugate Synthesis

A. Synthesis of Compound 51 Rha2-DPoPE

The method illustrated in Scheme 1 and further described below can be employed to prepare Rha2-conjugates with various phosphoethanolamine lipids. The method is exemplified with the lipid DPoPE.

Scheme 1

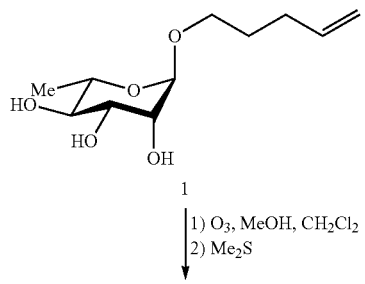

1
1) O$_3$, MeOH, CH$_2$Cl$_2$
2) Me$_2$S

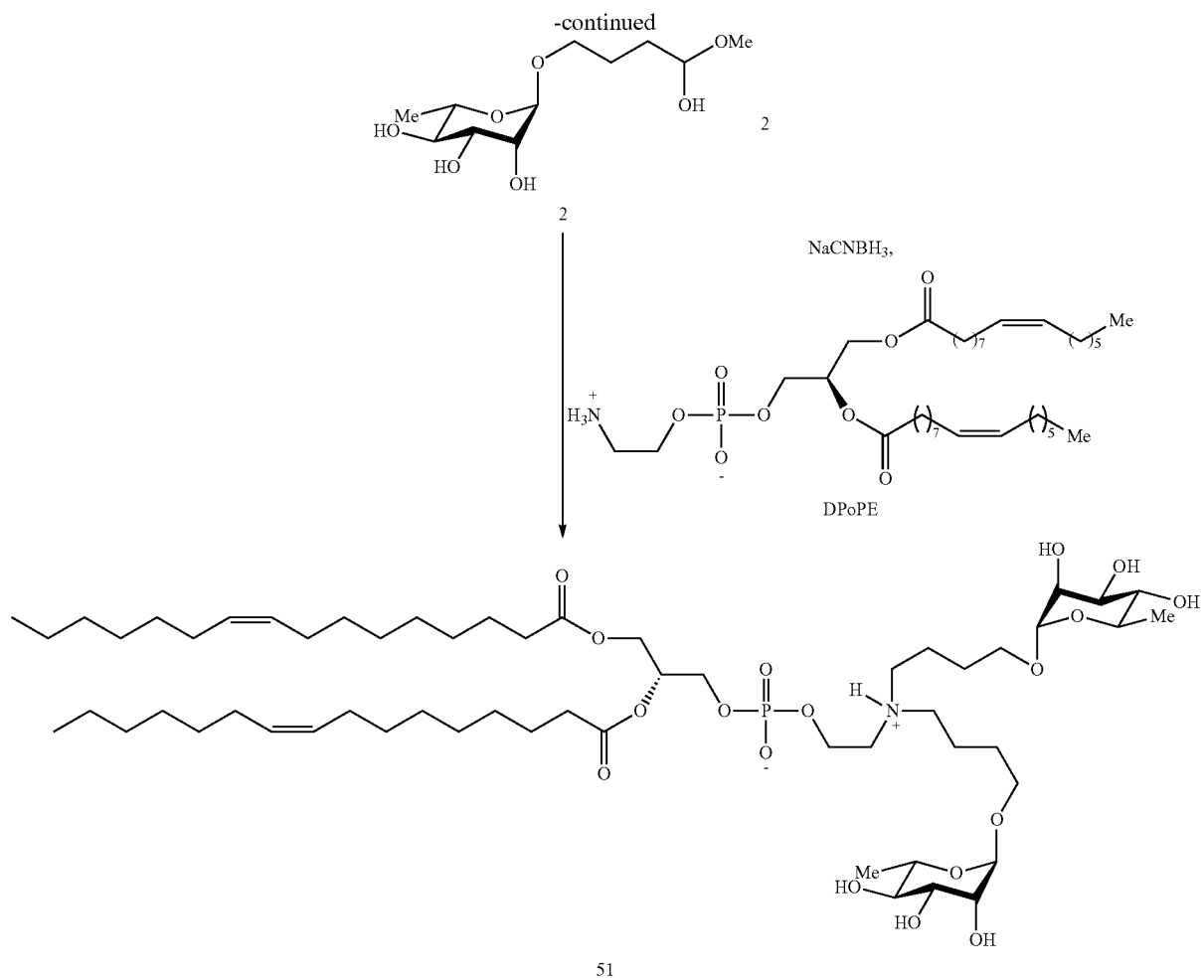

Compound 51 is synthesized as illustrated in Scheme 1. Compound 1 is synthesized according to Sarkar et al. (2010) J. Am. Chem. Soc. 132(48), 17236-17246. Compound 2 is synthesized according to a modification of the Sakar et al. procedure.

To a stirred solution of compound 1 (2.35 g, 10.1 mmol) in a mixture of methanol (10 mL) and dichloromethane (10 mL) were added 2.18 g of NaHCO$_3$. This suspension is cooled to −78° C. and ozone is then bubbled through the solution for 20 minutes, at which point a blue color persists in solution. The excess ozone is then flushed out of the reaction vessel by bubbling the solution with oxygen for 10 minutes, until the blue color is discharged. Then, dimethyl sulfide (3 mL, 40.8 mmol) is added to the reaction, which is left to warm to room temperature. The reaction is stirred for 36 hours, at which point TLC and $^{13}$CNMR confirm the complete reduction of the intermediate ozonide. The reaction is filtered, evaporated in vacuo and purified by silica gel chromatography using a gradient of 10→20% methanol in dichloromethane, yielding the desired hemiacetal product 2 as a colorless oil (2.10 g, 7.89 mmol, 78% yield). $^1$H NMR (300 MHz, Methanol-d4+Chloroform-d) δ 4.69 (d, J=1.8 Hz, 1H), 4.57 (s, 1H), 3.83 (dd, J=3.5, 1.7 Hz, 1H), 3.67 (dd, J=9.6, 3.4 Hz, 2H), 3.62-3.54 (m, 1H), 3.34 (s, 5H), 1.98-1.79 (m, 1H), 1.64 (dd, J=4.5, 2.5 Hz, 3H), 1.27 (d, J=6.3 Hz, 3H). $^{13}$C NMR (101 MHz, MeOD+CDCl$_3$) δ 100.24, 98.34, 72.61, 71.07, 70.95, 68.39, 66.92, 53.30, 33.30, 24.57, 16.62. MS (ESI) (observed as the free aldehyde) found: 378.1772 (M+NH$_{4+}$). calculated: 378.1759.

Compound 51 is prepared as follows. To a stirred solution of compound 2 (686 mg, 2.58 mmol) in chloroform (3 mL) and methanol (3 mL) is added 1,2-dipalmitoleoyl-sn-glycero-3-phosphoethanolamine (462 mg, 0.67 mmol, DPoPE). Then, NaCNBH$_3$ (173 mg, 2.75 mmol) is added to the reaction, which was stirred at 45° C. overnight. The following day, the reaction mixture is concentrated in vacuo and the residue is purified by silica gel chromatography using a gradient of 10→50% methanol in chloroform, yielding the desired product as a colorless foam (456 mg, 0.41 mmol, 61% yield). $^1$H NMR (400 MHz, Methanol-d4+Chloroform-d) δ 5.41-5.28 (m, 4H), 5.26 (dd, J=6.6, 3.3 Hz, 1H), 4.72-4.68 (m, 3H), 4.44 (dd, J=12.0, 3.2 Hz, 1H), 4.24-4.11 (m, 3H), 4.02 (t, J=6.1 Hz, 2H), 3.89-3.81 (m, 2H), 3.80-3.71 (m, 2H), 3.67 (dd, J=9.5, 3.4 Hz, 2H), 3.57 (dt, J=12.3, 6.2 Hz, 2H), 3.48 (dt, J=10.3, 5.7 Hz, 2H), 3.38 (t, J=9.4 Hz, 4H), 3.20 (t, J=7.5 Hz, 3H), 2.34 (dt, J=9.7, 7.4 Hz, 4H), 2.03 (q, J=5.4, 4.9 Hz, 8H), 1.86 (q, J=6.7 Hz, 3H), 1.71 (dt, J=15.1, 7.2 Hz, 3H), 1.62 (q, J=7.1 Hz, 4H), 1.42-1.19 (m, ~40H), 0.90 (t, J=6.6 Hz, 6H). $^{13}$C NMR (101 MHz, MeOD+CDCl$_3$) δ 173.77, 173.41, 129.75, 129.49, 100.11, 77.98, 77.66, 77.34, 72.65, 71.06, 70.73, 70.33, 70.25, 68.52, 66.21, 63.82, 63.77, 62.41, 59.49, 55.14, 53.56, 53.49, 48.82, 48.61, 48.40, 48.18, 47.97, 47.76, 47.54, 34.01, 33.85, 31.66, 29.57, 29.11, 29.07, 28.99, 28.96, 28.94, 28.81, 27.01, 26.96, 26.26, 26.17, 24.78, 24.73, 22.48, 21.01, 17.11, 13.57. MS (ESI) found: 1146.7059 (M+Na$^+$), calculated: 1146.7040.

B. Synthesis of Compound 4 Rha-DPoPE

Lipid conjugate 4, Rha1-DPoPE, is synthesized in an analogous manner to compound 51, but changing the stoichiometry of the amine and aldehyde.

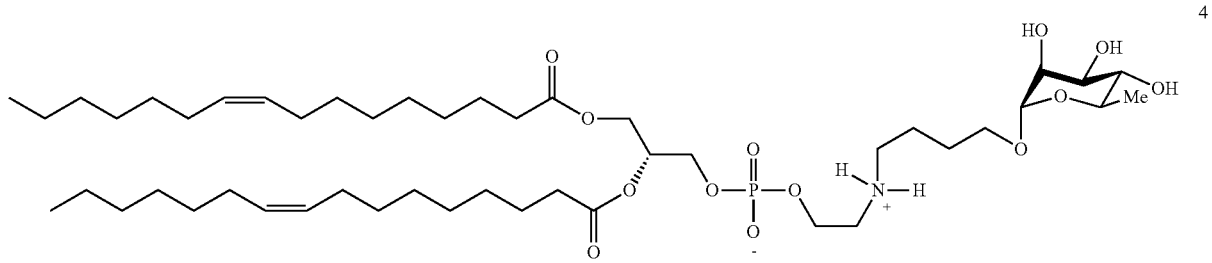

4

To a stirred solution of compound 2 (20 mg, 0.072 mmol) in chloroform (0.5 mL) and methanol (0.5 mL) is added 1,2-dipalmitoleoyl-sn-glycero-3-phosphoethanolamine (53 mg, 0.077 mmol). Then, NaCNBH$_3$ (8.4 mg, 0.134 mmol) is added to the reaction, which is stirred at 45° C. overnight. After 36 hours, more NaCNBH$_3$ is added to the reaction (13.4 mg) and the reaction is further reacted for 24 hours. The reaction mixture is concentrated in vacuo and the residue is purified by silica gel using a gradient of 10→50% methanol in chloroform. Then, the fractions containing the desired product are purified by reverse-phase chromatography on a C18 column using a gradient of 0→100% isopropanol in acetonitrile, yielding the desired product 4 as a colorless foam (19.6 mg, 0.022 mmol, 30% yield).

$^1$H NMR (500 MHz, Methanol-d4) δ 5.35 (td, J=6.9, 6.0, 3.8 Hz, 4H), 5.24 (dt, J=8.9, 4.1 Hz, 1H), 4.72 (d, J=1.7 Hz, 1H), 4.42 (dd, J=12.0, 3.2 Hz, 1H), 4.18 (dd, J=12.0, 6.7 Hz, 1H), 4.12-4.03 (m, 2H), 4.01 (t, J=6.0 Hz, 2H), 3.85 (dd, J=3.4, 1.7 Hz, 1H), 3.75 (dt, J=10.2, 5.9 Hz, 1H), 3.66 (dd, J=9.5, 3.4 Hz, 1H), 3.57 (do, J=9.4, 6.3 Hz, 1H), 3.45 (dt, J=10.3, 5.5 Hz, 1H), 3.39 (t, J=9.6 Hz, 1H), 3.17-3.11 (m, 2H), 2.99 (t, J=7.5 Hz, 2H), 2.33 (q, J=7.8 Hz, 4H), 2.02 (q, J=6.2 Hz, 8H), 1.79 (do, J=13.0, 6.4 Hz, 2H), 1.70 (h, J=6.7 Hz, 1H), 1.61 (p, J=6.7 Hz, 4H), 1.38-1.21 (m, ~36H), 0.89 (t, J=6.9 Hz, 6H).

$^{13}$C NMR (126 MHz, MeOD) δ 173.89, 173.50, 129.88, 129.59, 100.02, 77.64, 77.58, 77.38, 77.13, 72.61, 71.12, 70.63, 70.29, 70.23, 68.40, 66.46, 63.68, 63.64, 62.47, 60.84, 49.15, 49.03, 48.98, 48.86, 48.81, 48.69, 48.52, 48.35, 48.18, 48.01, 47.82, 34.11, 33.96, 31.84, 31.70, 29.62, 29.56, 29.27, 29.15, 29.12, 29.04, 29.02, 28.99, 28.88, 27.09, 27.04, 26.19, 24.80, 24.76, 23.84, 22.55, 17.24, 13.80. MS (ESI) found: 906.6063 (M+H+), calculated: 906.6067.

C. Synthesis of Lipid-Conjugate 52, Rha2-Cholesterol

Lipid conjugate 52 is synthesized as illustrated in Scheme 2 from starting materials 5, 6, and 7 and the exemplary sterol, cholesterol, which are available from natural sources, commercial sources or which can be prepared by methods that are well-known in the art. Intermediate protected-rhamnose2-cholesterol 8 is DE protected with Leo and purified by ion chromatography to provide Rha2-cholesterol 52. This method can be employed to prepare Rha2-conjugates with various sterols, particularly sterols having a 3-OH, and more particularly a 3β-OH. Specific sterols include cholesterol, desmosterol, lanosterol, zymosterol, coprostanol, lathosterol, zymostenol, dormatinol and substituted derivatives of sterols, including among others mono- and dihydroxy substituted derivatives of sterols, e.g., 1-hydroxy, 4-hydroxy, 6-hydroxy, 7-hydroxy, 22-hydroxy, 24-hydroxy, 25-hydroxy, 27-hydroxy, 5,6-dihydroxy, or 1,25-dihydroxy substituted sterols, particularly where the sterol is cholesterol; oxo-substituted sterols, e.g., 7-oxo-substituted sterols, for example 7-oxocholesterol, dehydro derivatives of sterols, e.g., 7-dehydrocholesterol, or dihydro derivatives of sterols, e.g., dihydrocholesterol.

Scheme 2-1

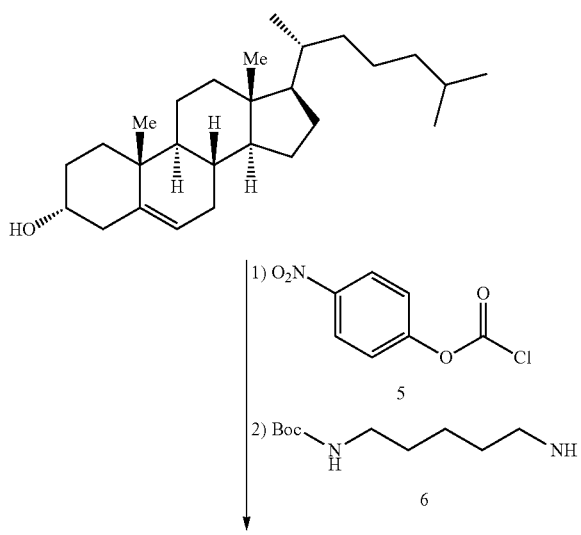

-continued

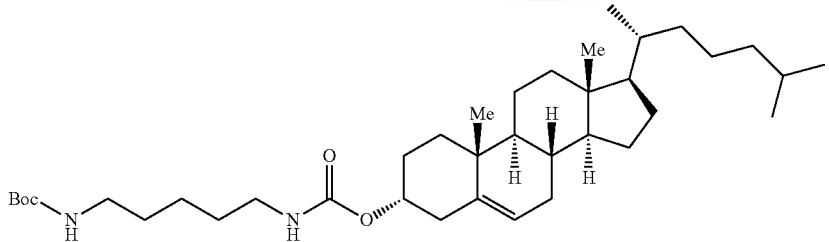

1) TFA
2) NaCNBH₃

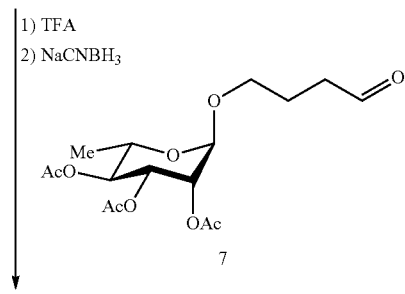

7

Scheme 2-2

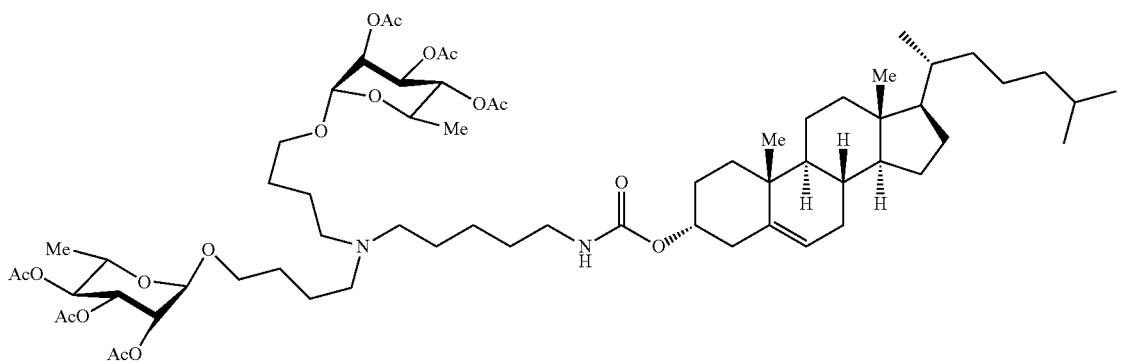

8

1) LiOH
2) ion exchange

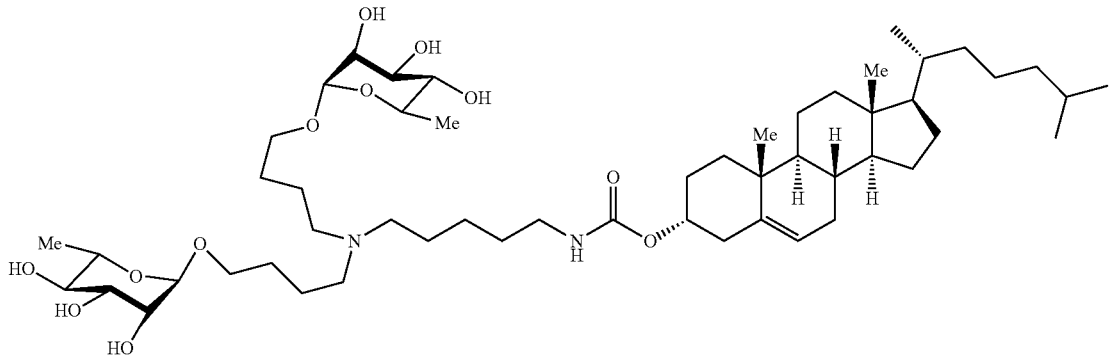

52

D. Synthesis of Lipid Conjugate Rha2-Ceramide

Lipid conjugate 53 is synthesized as illustrated in Scheme 3 from starting materials 5, 6, and 7 and the exemplary ceramide Cer1, where n is an integer from 7-32 and specifically is 11-22 and more specifically is 12 and where m is an integer ranging from 6 to 20, and specifically m is 9-12 and more specifically m is 11. Intermediate protected-rhamnose2-ceramide 10 is deprotected with LiOH and purified by ion chromatography to provide Rha2-ceramide 53. This method can be employed to prepare Rha2-conjugates with various ceramides, which may be naturally-occurring from plant, animal, or microbial sources and in a specific embodiments with ceramides of formula CerX. Ceramides are available from natural sources, commercial sources or can be prepared by chemical synthetic methods or enzymatic methods that are well-known in the art employing readily available starting materials. See for example U.S. Pat. No. 7,344,868; 5,610,040 or 5,525,709.

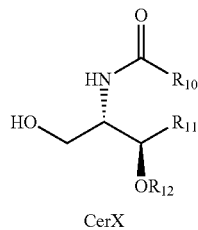

CerX where:

$R_{10}$ is an alkyl or alkenyl group having 8-32 carbon atoms, wherein the alkenyl group can have one or more double bonds and wherein the alkyl group can be substituted with 1-6 OH groups;

$R_{11}$ is an alkyl or alkenyl group having 7-24 carbon atoms, wherein the alkenyl group can have one or more double bonds and wherein the alkyl group can be substituted with 1-6 OH groups; and $R_{12}$ is H, a alkyl group having 1-3 carbon atoms or an art-recognized protecting group, such an acyl group, e.g., $CH_3$—CO—.

Scheme 3-1

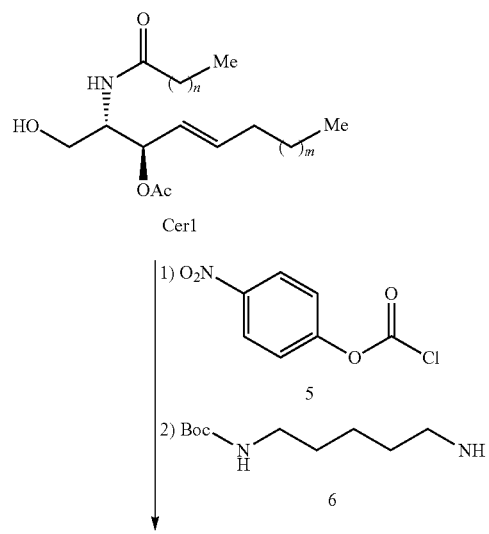

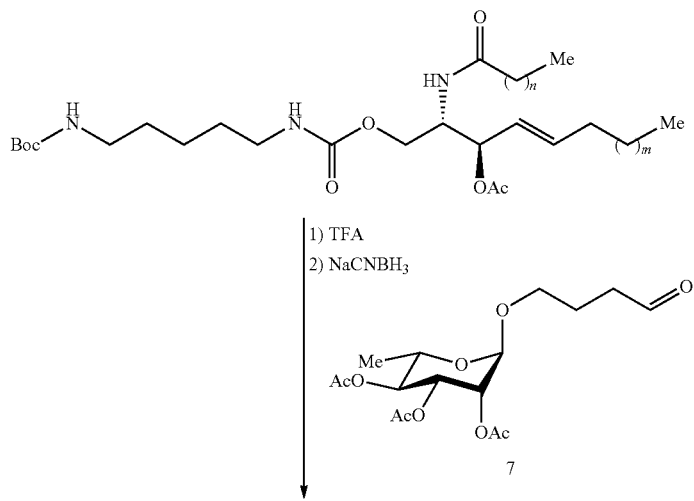

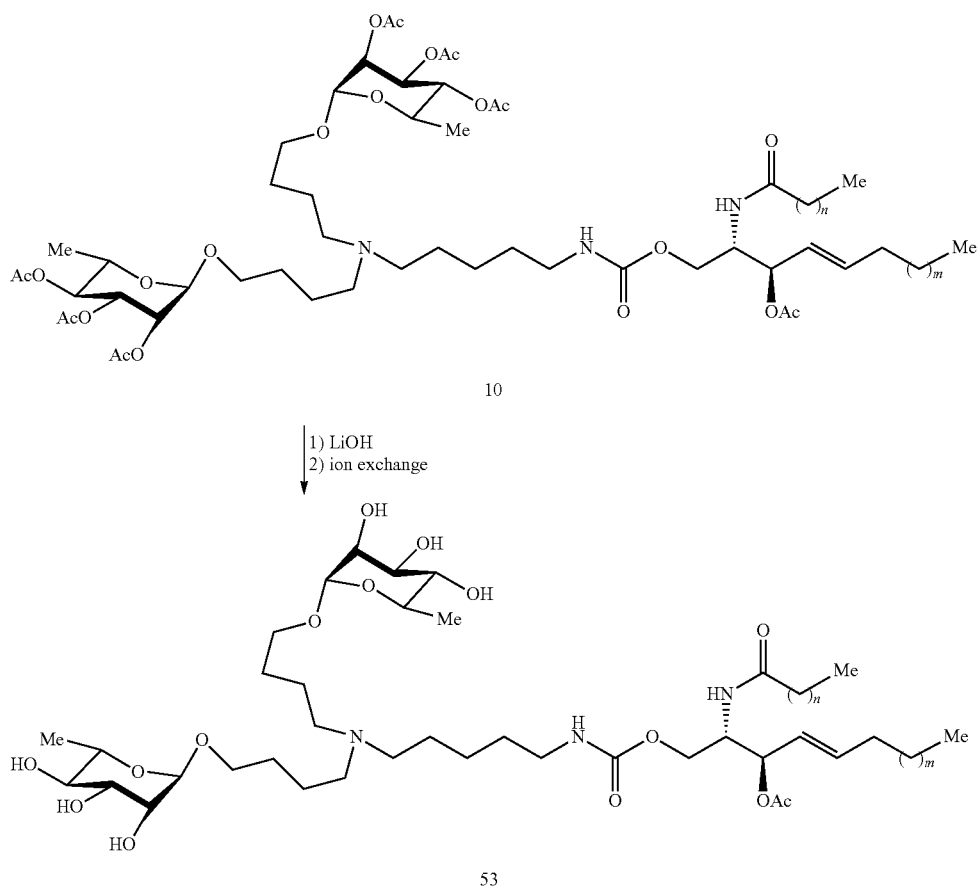

10

53

E. Synthesis of Rh4-Lipid Conjugate 54

The method illustrated in Scheme 4 can be employed to prepare Rha4-conjugates with various lipids, particularly with phosphoethanolamine lipids, ceramides and sterols, and most particularly with phosphoethanolamine lipids.

Lipid conjugate 54 is synthesized as illustrated in Scheme 4 from starting materials 12, 1 and 2 and the exemplary phosphoethanolamine (DPoPE) which are available from commercial sources or which can be prepared by methods that are well-known in the art. The lipid is coupled to a protected diaminocarboxylic acid, such as Fmoc-protected lysine 12, employing, for example a uronium coupling reagent such as HATU to generate the lipid intermediate 14. This reaction functions to attach a multivalent linker (the amino groups of the linker are later used to attach rhamnose moieties) to the lipid. Excess of the rhamnose derivative 2 is then conjugated to lipid intermediate 14 to form lipid conjugate 54 which carries 4 rhamnose monosaccharide moieties.

Scheme 4

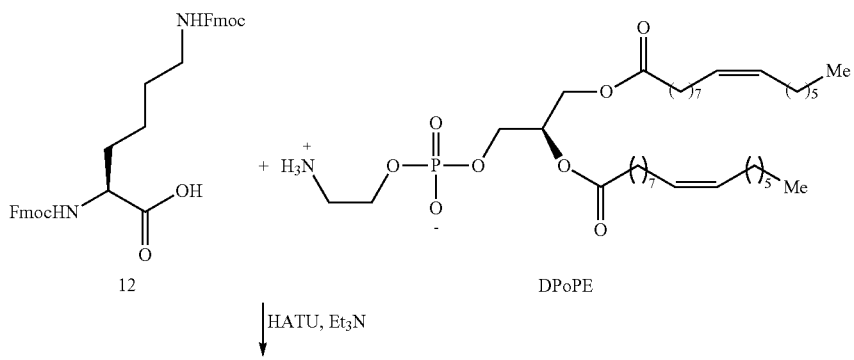

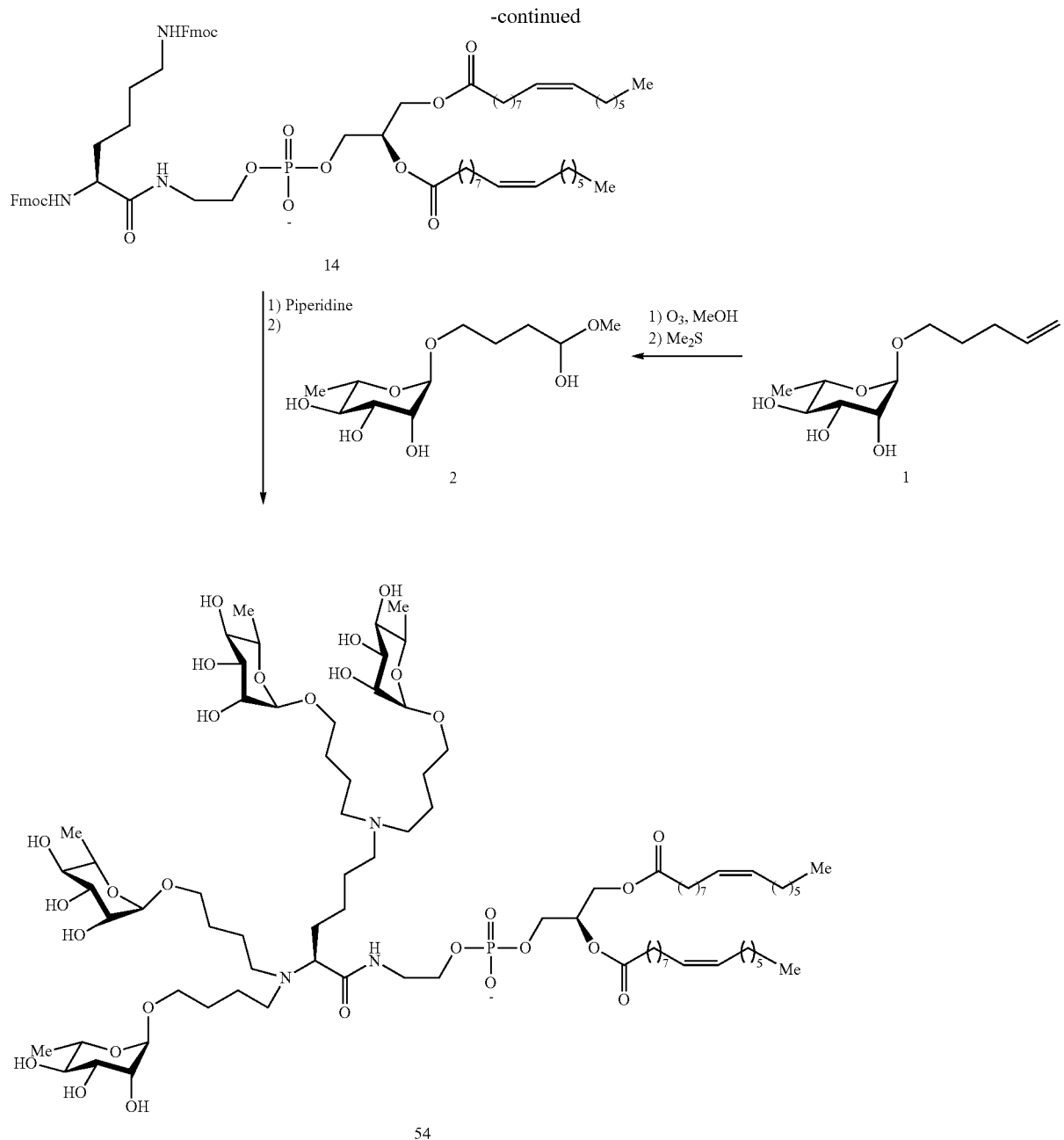

HATU = 2-(1H-7-Azabenzotriazol-1-yl)--1,1,3,3-tetramethyl uronium hexafluorophosphate Methanaminium F. Synthesis of 8-Rha-Lipid Conjugate 55

Scheme 5 illustrates how the method of Scheme 4 can be expanded to prepare lipid conjugates carrying additional rhamnose monosaccharide moieties. Again this expanded method can be employed to prepare 8 Rha or higher Rha-conjugates with various lipids, particularly with phosphoethanolamine lipids, ceramides and sterols, and most particularly with phosphoethanolamine lipids.

Lipid conjugate 55 is synthesized as illustrated in Scheme 5 from starting materials 12, and 2 and the exemplary phosphoethanolamine lipid (DPoPE) which are available from commercial sources or which can be prepared by methods that are well-known in the art. The lipid is coupled to a protected diaminocarboxylic acid, such as Fmoc-protected lysine 12, employing, for example a uronium coupling reagent such as HATU to generate the lipid intermediate 14. This reaction functions to attach a multivalent linker (the amino groups of the linker are later used to attach rhamnose moieties) to the lipid. A second coupling of a protected diaminocarboxylic acids, such as Fmoc-protected lysine 12, results in a linker having capacity to couple to 8 rhamnose moieties as illustrated. Excess of the rhamnose derivative 2 is then conjugated to lipid intermediate 16 to form lipid conjugate 55 which carries 8 rhamnose monosaccharide moieties. It will be appreciated by one of ordinary skill in the art that additional rounds of coupling of the diaminocarboxylic acid can be employed to increase the valency of the linker to the lipid and allow for coupling to additional rhamnose moieties. The concept employed is based on a dendron generation and as illustrated 16-Rha-lipid conjugates, 32-Rha-lipid conjugates and higher order Rha-lipid conjugates can be synthesized. See for example, Klok H-A. et al. Self-Assembling Biomaterials: I-Lysine-Dendron-Substituted Cholesteryl-(I-lactic acid)$_n$ Macromolecules 2002 35 (16), 6101-611.

As an alternative, a multivalent linker carrying a plurality of rhamnose moieties can be prepared using coupling reactions that are well-known in the art. Thereafter the preformed rhamnose-containing species can be conjugated to a desired lipid again using well-known methods. For example, amine groups of a dendron or dendrimer, structures that are well-known in the art, can be coupled to a desired number of rhamnose moieties and the resulting rhamnose-coupled dendron or dendrimer can thereafter be conjugated to a selected lipid. An overview of chemical methods applied to synthesis of and conjugation to dendrimers and dendrons is provided in Newkome, G. R. et al. (2004) *Dendrimers and Dendrons: Concepts, Syntheses, Applications* Wiley-VCH Verlag GmbH& Co. See also Hermanson, G. (2008) Bioconjugation Techniques Part II, "Dendrimers and Dendrons" Academic Press/Elsevier, Chapter 7, pages 346-389.

Scheme 5-1

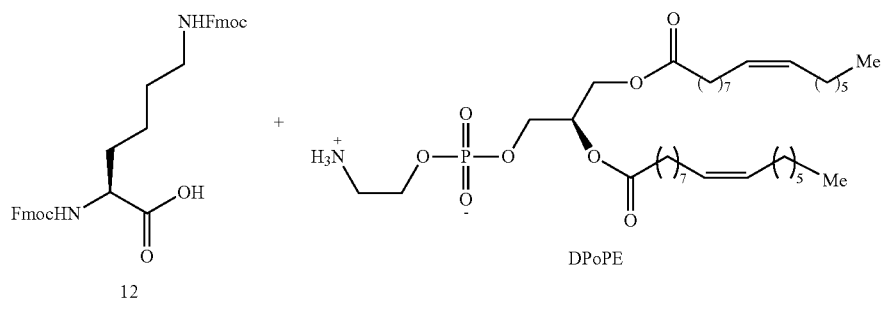

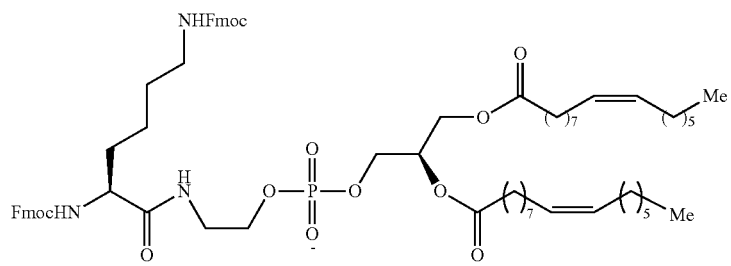

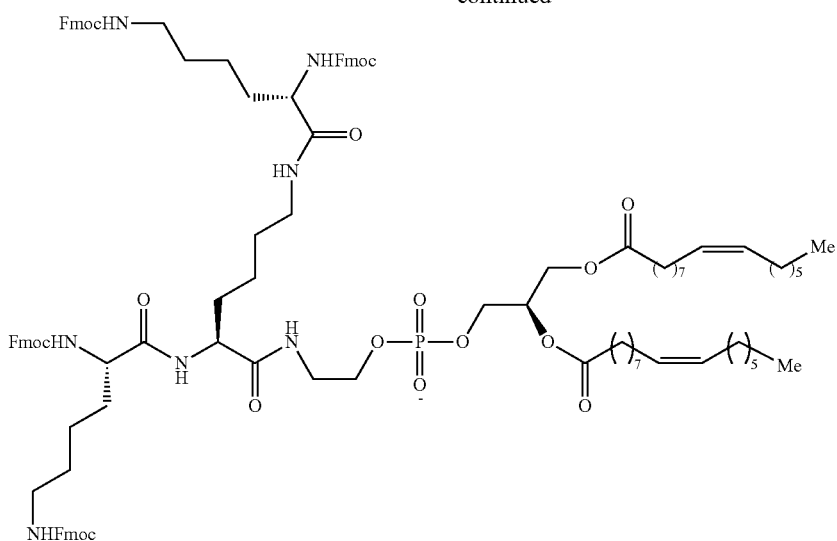
16
Scheme 5-2
1) piperidine
2) NaCNBH₃,
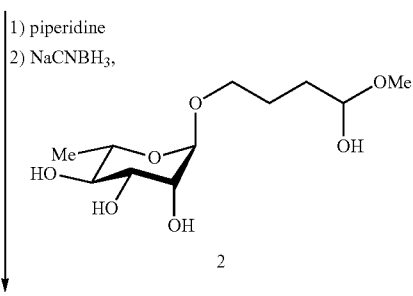
2
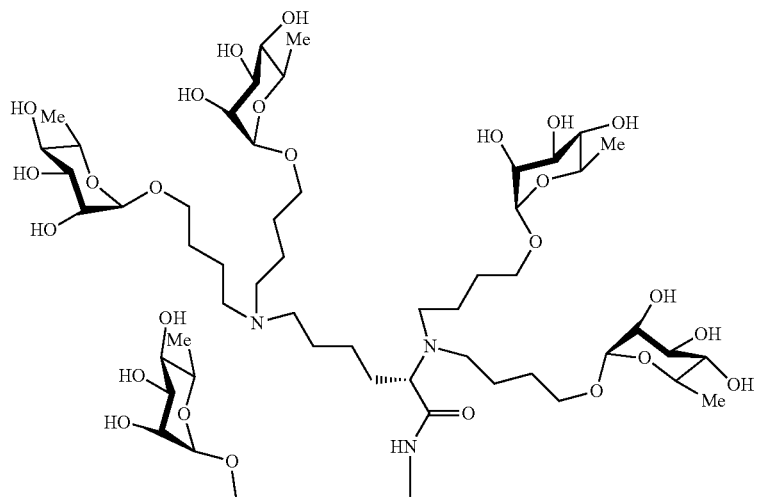

-continued

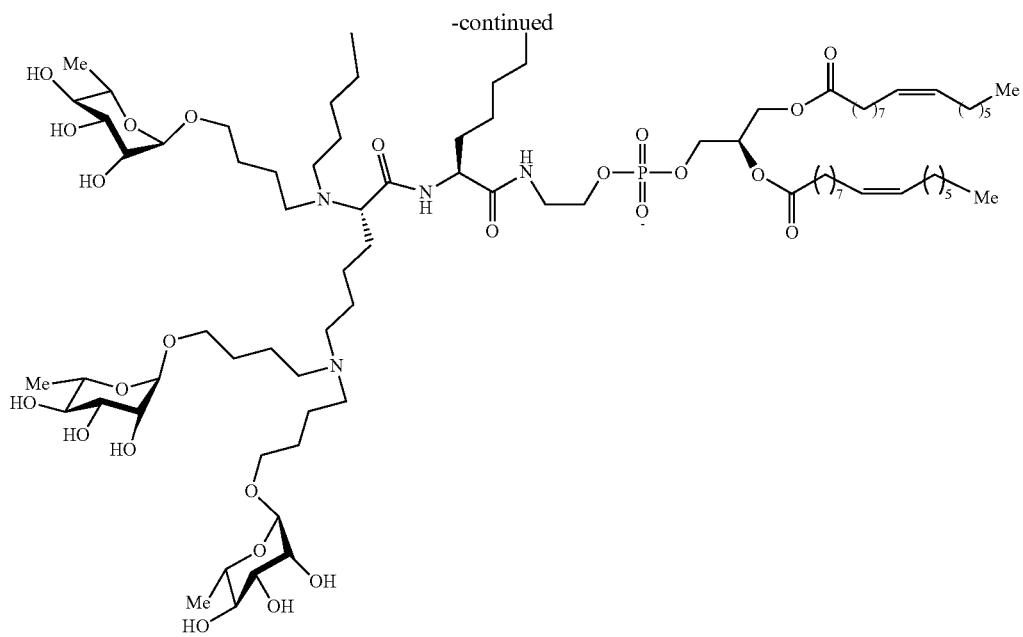

55

Example 2: Rhamnose Antibodies in Human Serum

Biosensor analysis was used to evaluate levels of antibodies in human serum. Surface plasmon resonance (SPR) is an information-rich technique requiring only small amounts of material, and surfaces with immobilized compounds can be regenerated and used multiple times. Although this technique is most often associated with determination of kinetic parameters, it is also useful for rank ordering interactions with ligands and antibody characterization, and is compatible with serum. Biotinylated αGal (Gal-α-1,3-Gal), rhamnose, and DNP (2,4-dinitrophenol) were synthesized using a spacer of at least twelve ethylene glycol units between the antigen and biotin moiety, to ensure that the antigen would remain accessible to antibodies even when the biotin moiety was bound to immobilized streptavidin. The biotinylated antigens were immobilized on streptavidin-coated sensor chips along with a biotinylated control peptide in a reference channel. Serum was collected from healthy volunteer donors under IRB-approved Human Subjects minimal risk protocol M-2005-1282 at the University of Wisconsin-Madison.

Figure 2A:
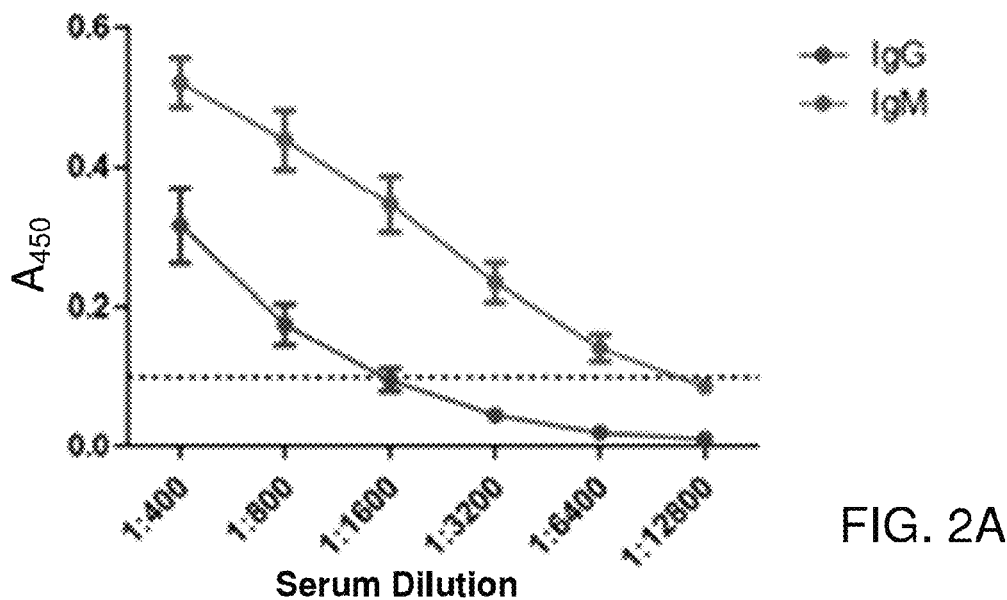
FIGS. 2 A-C are three graphs presenting the results of ELISA assays of three serum samples labeled 1, 3 and 4, respectively. The ELISA assays used immobilized rhamnose-BSA conjugates to indicate the relative amounts of IgG and IgM antibodies to L-rhamnose with dilution of human serum. Antibodies to rhamnose are from both IgM and IgG pools. The antibodies are mostly IgM, however titers of IgG are reasonably good particularly in serum samples 1 and 3.
Figure 2B:
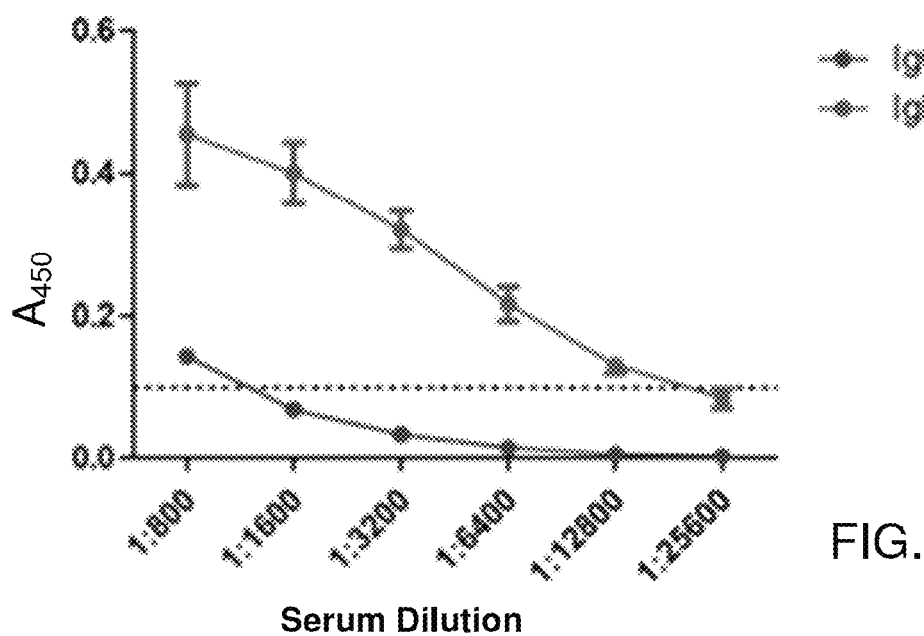
Figure 2C:
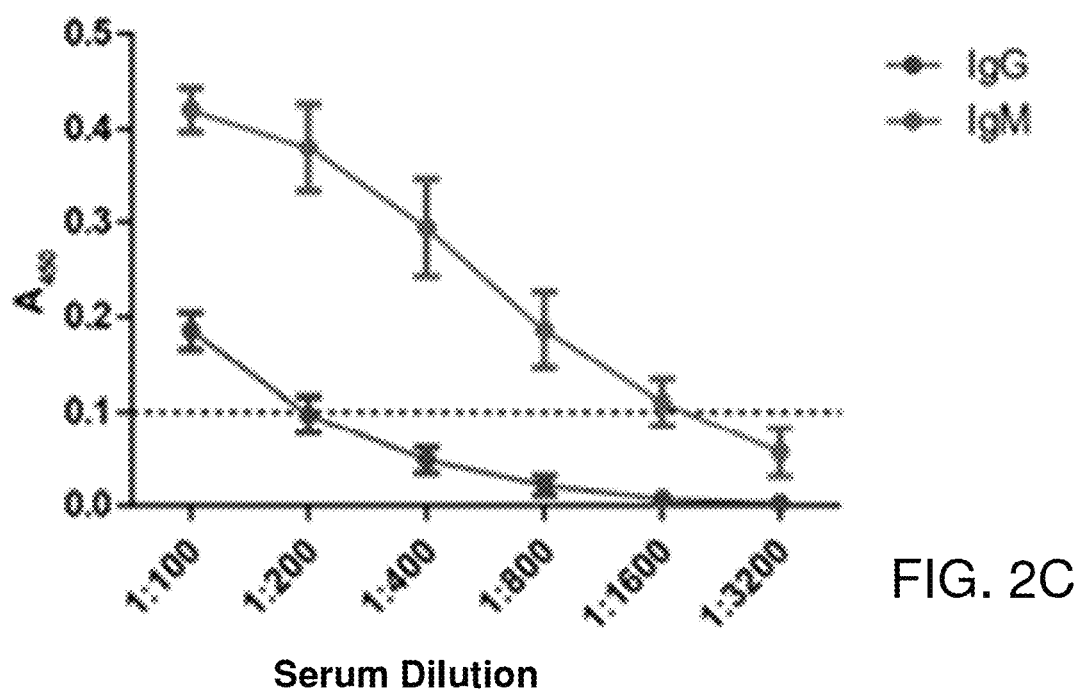

To limit bulk refractive index changes and keep signal within the instrument's detection range, solutions of 10% serum were flowed across the chip, contacting antigens in this order: DNP, αGal, rhamnose, reference channel. As a measure of antibody prevalence, corrected response units ($RU_{antigen}$-$RU_{reference}$) bound to each flow channel were compared after 5 minutes of serum exposure; more RU indicated greater antibody binding and therefore, a higher titer. Antibodies recognizing rhamnose were more prevalent than those recognizing αGal in all cases, and were equivalent or better to those recognizing DNP in most cases (FIG. 1). Antibodies to rhamnose were further assessed with ELISA assays using immobilized rhamnose-BSA. Antibodies to rhamnose were found from both the IgG and IgM pools suggesting that these antibodies would be able to activate both complement- and cell-mediated pathways (FIGS. 2A-C).

Example 3: Stability of Antigen-Antibody Complexes

Figure 3:
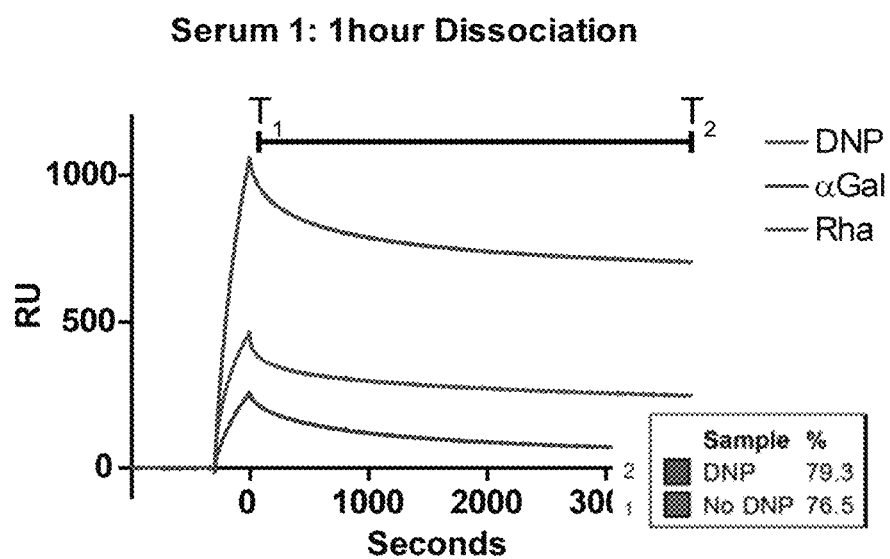
FIG. 3 illustrates a graph monitoring loss of binding signal over the course of one hour for antigen-antibody complexes for DNP, αGal and Rha in a serum sample.

The relative stability of antigen-antibody complexes for DNP, αGal and Rha in serum was assessed by evaluating RU (corrected RU) as a function of time (over 1 hour). FIG. 3 illustrates the decay of RU with time for antigen-antibody complexes for the three antigens. Due to the complexity of these systems, exact kinetic parameters could not be determined; however the loss of response units over time provides an estimate rank ordering of dissociation rates and complex longevity. In most cases, signal loss was greater for αGal and DNP than for rhamnose over the time course of one hour indicating that the rhamnose-anti-rhamnose complexes have an affinity advantage over those of both αGal and DNP. More stable antigen-antibody complexes are expected to have a greater chance of forming productive interactions with complement proteins and effector cell receptors.

Example 4: Antigen-Lipid Insertion into Cell Membranes

Figure 4:
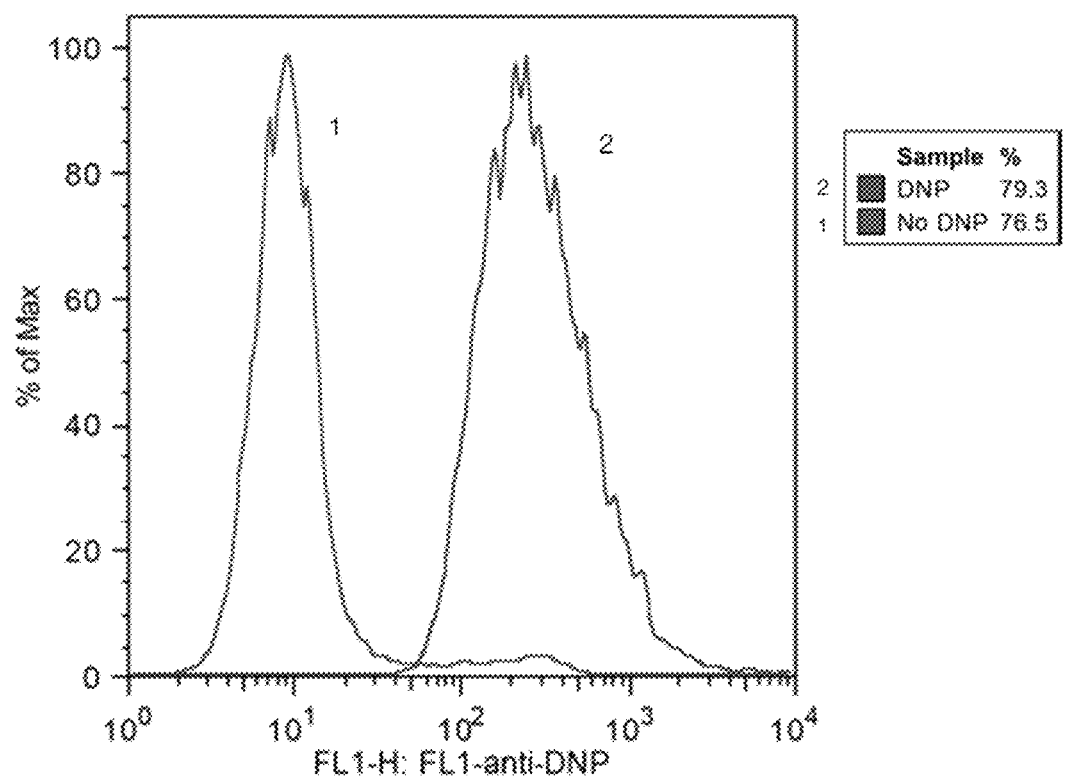
FIG. 4 is a graph showing the results of flow cytometry measurement of M21 cells treated with or without DNP-lipid and stained with anti-DNP. DNP-lipid 100 (Avanti Polar Lipids, Alabaster, Ala.) was used for the experiment. The shift for cells treated with DNP-lipid indicates that the antigen headgroup is not hidden from the antibody. The results indicate that antigens headgroups of the antigen-lipid conjugates remain accessible to antibodies after insertion of the conjugate into cells.

As an initial assessment of antigen-lipid insertion into cell membranes, a hapten-lipid conjugate, DNP-lipid (100, a dipalmitoleoyl phosphatidylethanolamine-DNP conjugate) and anti-DNP-antibody were used to determine if (1) lipids would insert into model M21 cell line and (2) if the antigen headgroups of the antigen-lipid conjugates would remain accessible to antibodies. M21 cells treated with the DNP-lipid followed by staining with anti-DNP were analyzed by flow cytometry (FIG. 4). The positive shift observed indicated that the lipids had successfully inserted into the cell membrane and that antigen head groups were accessible to antibody.

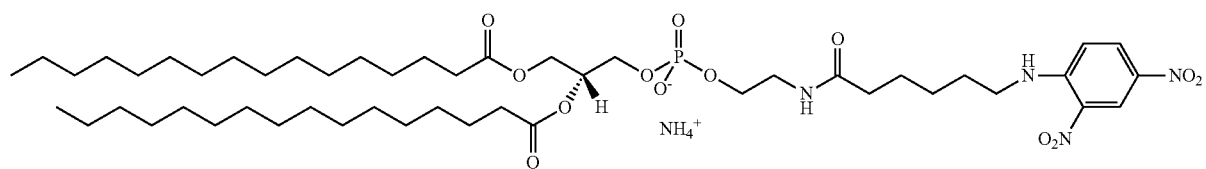

100

To estimate lipid insertion levels into model cells, three fluorescent lipid derivatives were synthesized: 101 an Alexa-Fluor® 488 dye conjugated to cholesterol, 102 Alexa-Fluor® 488 dye (Life Technologies) conjugated to POPE and 103 an Alexa-Fluor® 488 dye conjugated to DPoPE.

Figure 5:
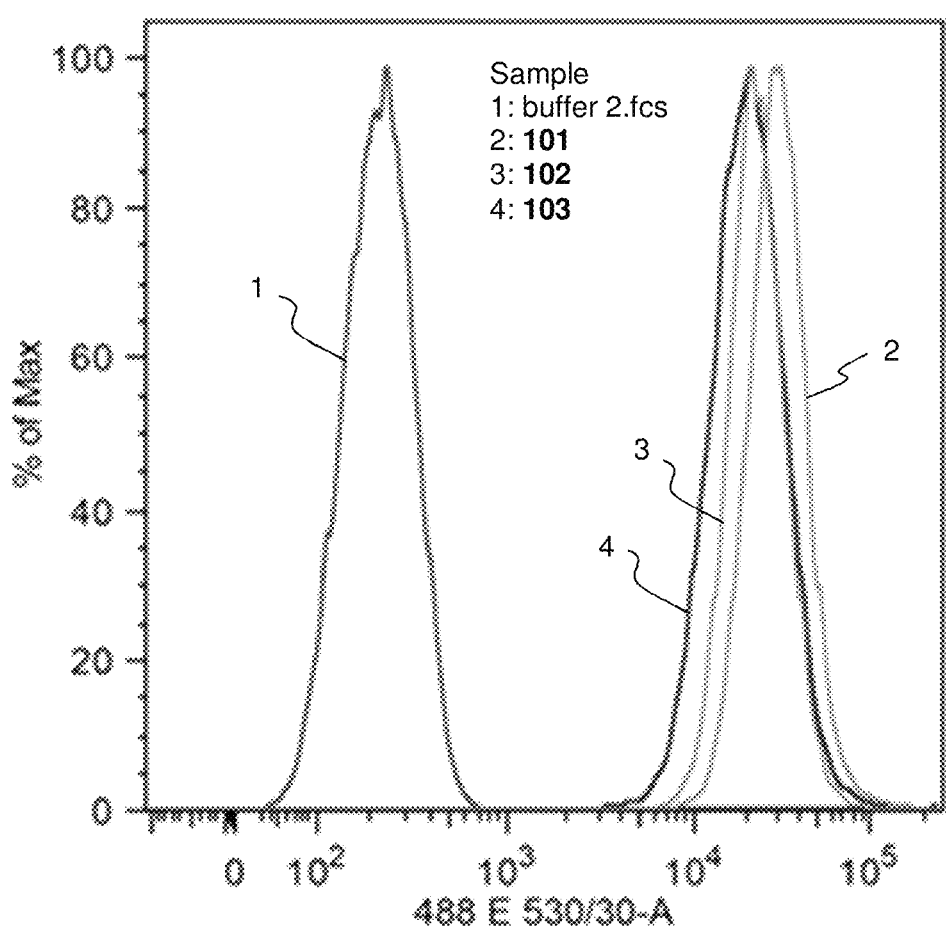
FIG. 5 is a graph showing the results of flow cytometry measurements to assess the levels of insertion of fluorescent lipid conjugates into M21 cells. See Example 4 and Scheme 6 for details. Under the treatment conditions used, insertion levels of approximately $3\times10^6$ lipids per cell was achieved. All three fluorescent labeled lipids inserted robustly into the cell membrane.

M21 cells were treated with these lipids and assessed by quantitative flow cytometry using calibration beads to determine the number of fluorophores per cell. The results are illustrated in FIG. 5. All three lipids showed robust insertion into cell membranes with copy numbers around $3 \times 10^6$.

Scheme 6

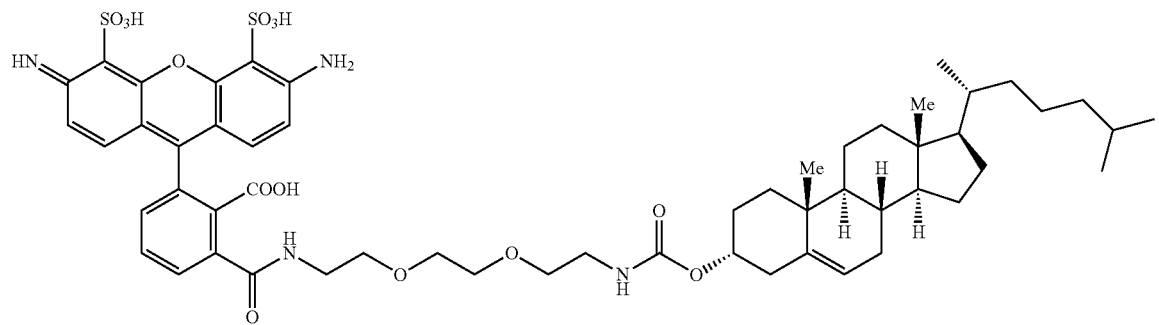

101

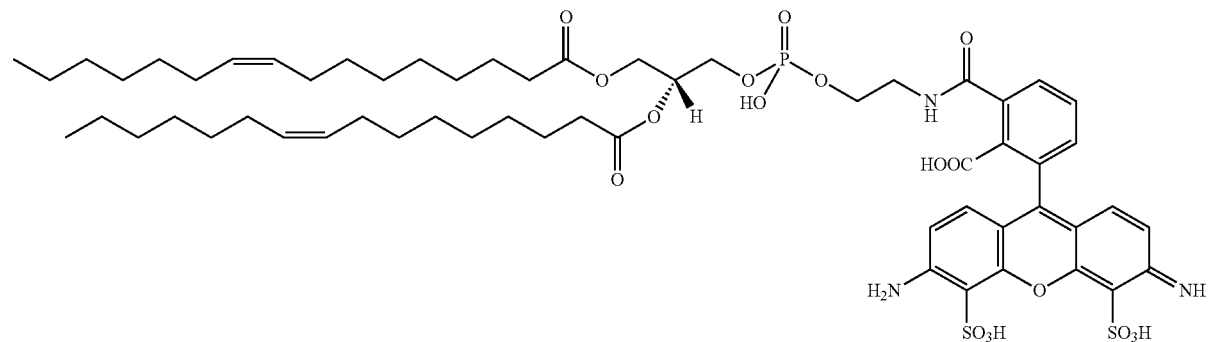

102

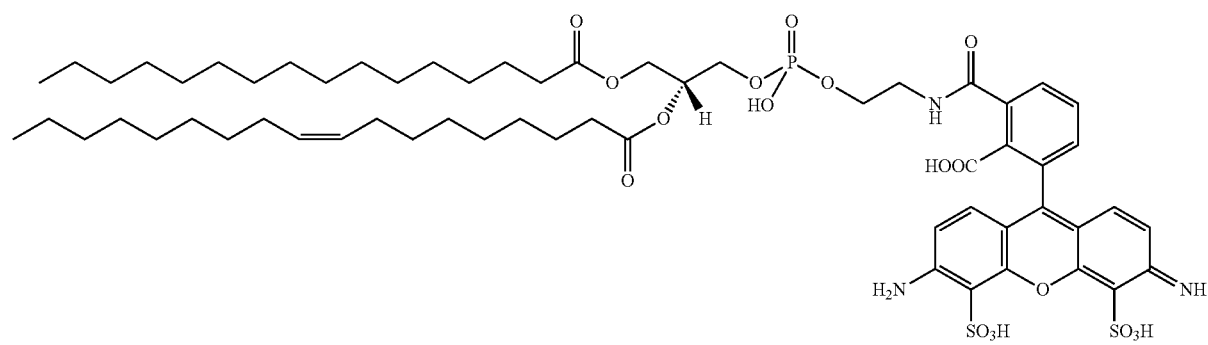

103

Example 5: Activation of Complement by Rhamnose-Lipid Conjugates

Figure 6:
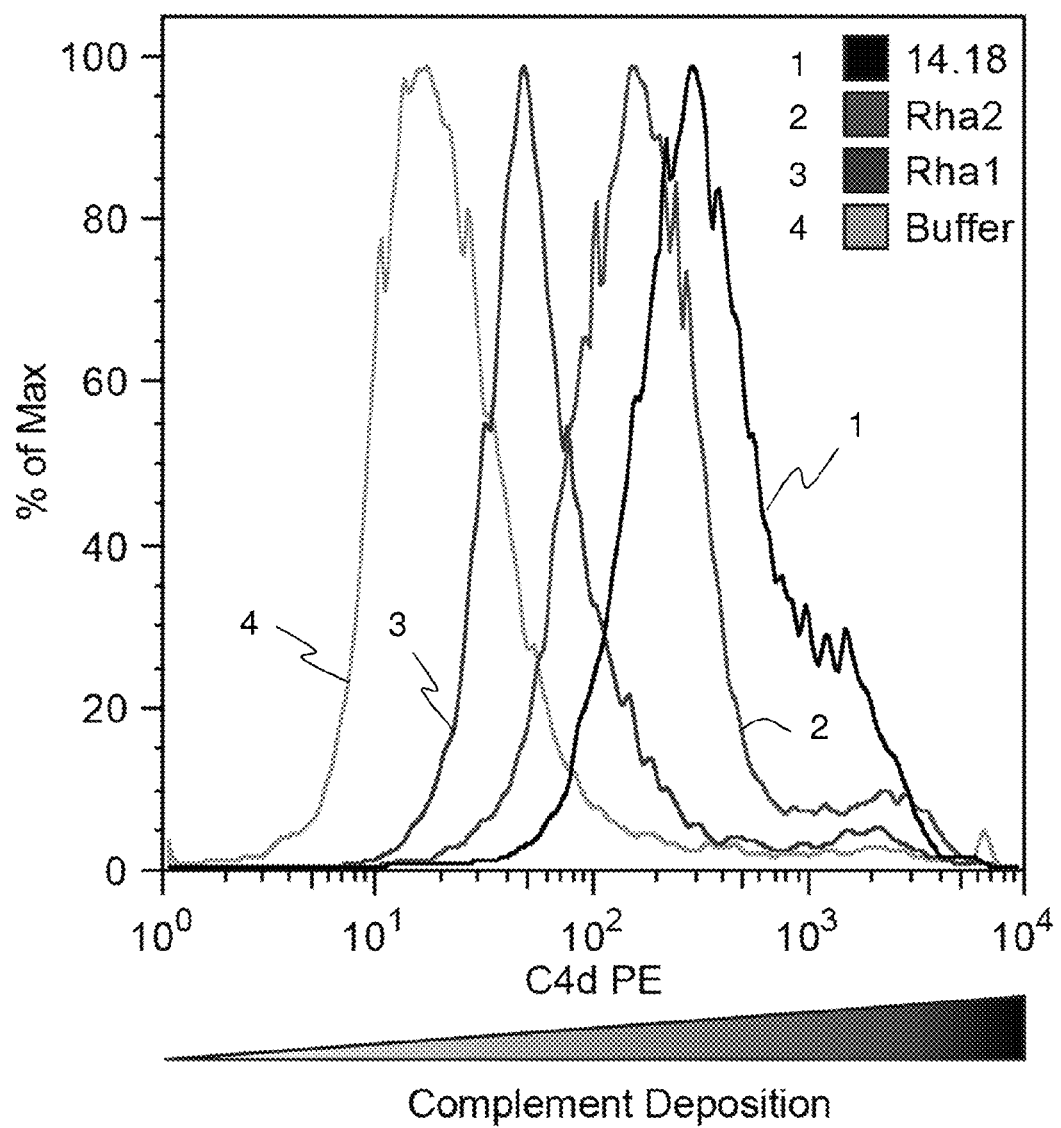
FIG. 6 is a graph showing the results of flow cytometry measurements of M21 cells treated with the indicated rhamnose-lipid conjugates, or with an antibody known to activate complement (14.18) exposed to normal human serum and subsequently stained for C4d, a marker of complement activation. Both mono- and di-rhamnose conjugates can activate the complement pathway, however, the di-rhamnose conjugate activates complement significantly more efficiently.

Rhamnose-lipid conjugates 4 (Rha1-DPoPE) and 51 (Rha2-DPoPE) were synthesized as described in Example 1. The ability of these compounds to activate complement was tested by looking for deposition of complement component C4d. M21 cells treated with buffer, $rha_1$-DPoPE, $rha_2$-DPoPE, or a control antibody known to activate complement (14.18) were exposed to 25% normal human serum for 1 hour at 37° C., washed and stained for C4d, and analyzed by flow cytometry. $Rha_1$-DPoPE and $rha_2$-DPoPE both activated complement with $rha_2$-DPoPE being more efficient (FIG. 6). The 14.18 antibody employed was the Ch14.18-IL2 fusion protein [Gillies, S D; Lan, Y; Lo, K M; Super, M; Wesolowski, J (1999) "Improving the efficacy of antibody-interleukin 2 fusion proteins by reducing their interaction with Fc receptors." Cancer Research vol. 59 (9) p. 2159-66.]

Example 6: Complement-Mediated Cytotoxicity Assay

Lipid Preparation:

The requisite amount of chloroform solution containing each lipid compound was measured into a glass vial. Chloroform was removed by blowing argon into the vial until all solvent was evaporated leaving a lipid film on the glass. The lipid film was hydrated with sufficient buffer (HBSS with 1% BSA) to yield a 0.1 mM solution for 30 minutes at room temperature. The vials were then sonicated in a water bath sonicator to cause the lipids to sheet off of the glass. It is believed that the lipids form vesicle structures in the buffer.

The lipids samples can be processed by various known lipid preparation methods, such as extrusion, to form more uniform lipid structures, including liposomes, without detrimental effects on cell membrane insertion.

Cell Treatment:

M21 cells were plated in a 12-well plate and allowed to grow over night. The next morning, the growth medium was removed and replaced with 0.5 mL of buffer (control) or lipid suspension. Cells were incubated in contact with lipids for 1 hour at 37° C. to allow for lipid insertion. The lipid suspension was then aspirated and cells were striped from the plate with 1 mM EDTA in PBS pH 7.4. The EDTA/cell suspensions were diluted ~1:1 with HBSS/BSA buffer, spun down and resuspended at 500,000 cells $mL^{-1}$. Cell samples where CD55 and CD59 were to remain functional were diluted 1:1 in HBSS/BSA buffer. Cell samples in which complement inhibitory factors were to be blocked were diluted 1:1 with HBSS/BSA containing 20 µg/mL of each blocking antibody (anti-CD55: clone 143-30 from Southern Biotech, anti-CD59: clone MEM-43 from Novus Biologicals) for a final concentration of 10 µg/mL of each antibody.

Figure 7:
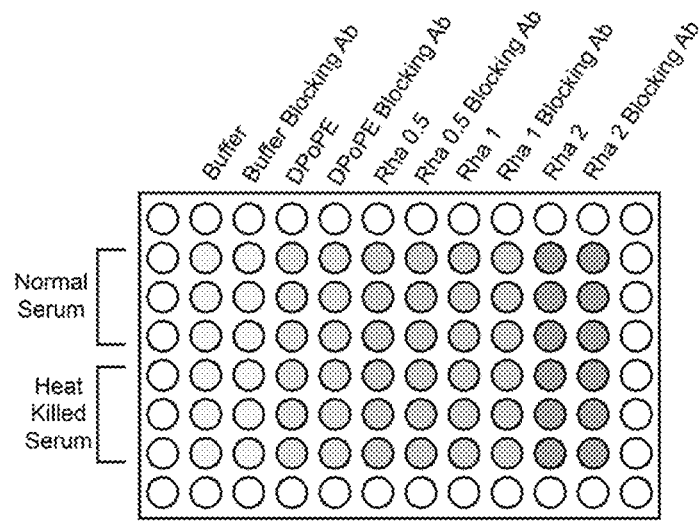
FIG. 7 is the plate illustration for Example 6. Each well had 12,500 cells from the specified treatment and 25% of either normal or heat killed serum. Wells with blocking antibodies also have 10 μg/mL of each antibody as described in Example 6.

Assay Plate:

Cell suspensions (50 µL) were added to an opaque white 96-well plate in sextuplicate. Thereafter, 50 µL of either 50% normal serum or 50% heat-inactivated human serum (where antibodies are functional, but complement proteins do not function) were added to the wells in triplicate. (See plate illustration FIG. 7.) The plate was incubated at 37° C. for two hours to allow for complement activation and cell killing. After 2 hours, the plate was removed from the incubator and allowed to come to room temperature. At this point, 100 µL of Cell Titer-Glo® reagent (Promega) was added to each well. Luminescence was read on a Tecan M1000 plate reader.

Data Analysis:

Luminescence values were averaged for each set of triplicate wells. Since luminescence correlates to viable cells and the heat killed serum wells provide a measure of non-specific cell death, the fraction of viable cells for each condition is calculated as (avg. $luminescence_{normal\ serum}$)/(avg. $luminescence_{heat\ killed\ serum}$). This value can be subtracted from 1 to obtain the fraction of dead cells and converted to a percentage (% cytotoxicity).

Figure 8:
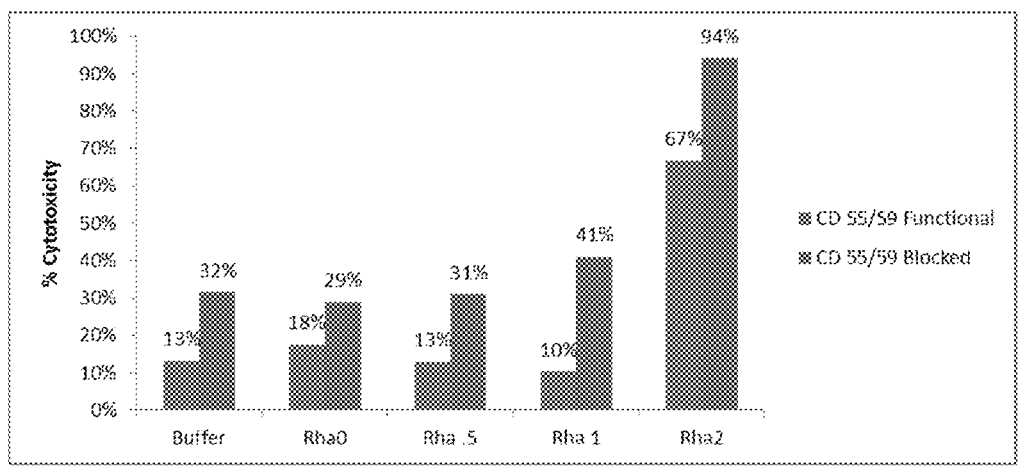
FIG. 8 is a graph of exemplary complement-mediated cytotoxicity results with rhamnose-lipid conjugates with DPoPE lipid.

FIG. 8 is a graph of % cytotoxicity with functional or blocked CD55 and CD59 after incubation of cells with lipid (no rhamnose, Rha0), lipid conjugate 4 (Rha1-DPoPE with a single rhamnose), and lipid conjugate 51 (Rha2-DPoPE) with two rhamnose. Lipid labeled Rha 0.5 is a 1:1 mixture of parental DPoPE lipid (Rha0) and Rha1-lipid 4. As shown in FIG. 8, the dirhamnose lipid 51 mediates cytotoxicity; however the monorhamnose lipid conjugate 4 does not. These results are consistent with experiments measuring the extent of complement activation FIG. 6. Additionally, the results show that preventing complement inhibitory factors CD55 and CD59 from functioning enhances cytotoxicity.

Figure 9:
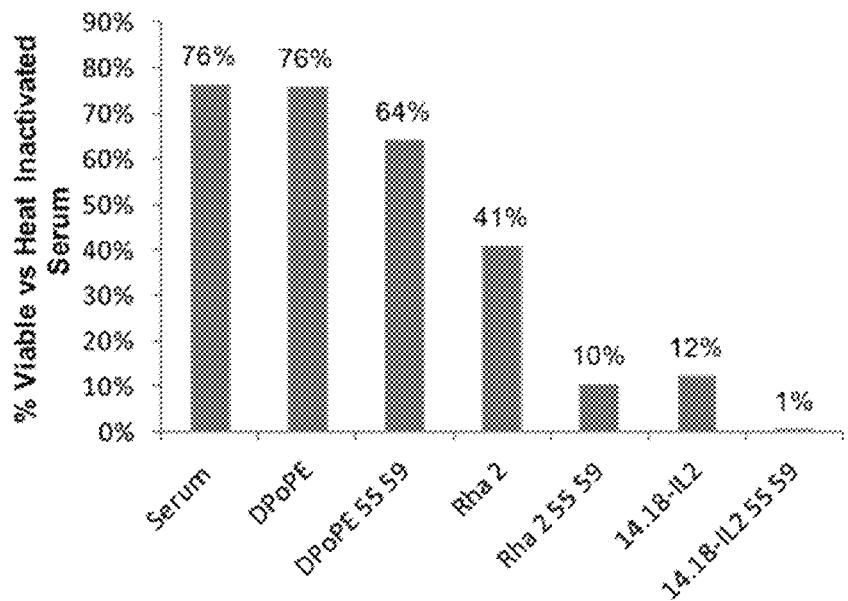
FIG. 9 is a graph comparing % viability of M21 cells treated as indicated, see Example 6.

FIG. 9 is a graph presenting results in terms of % viable cells for an experiment conducted with M21 cells as noted above which compared treatment of cells with lipid alone serum alone (negative control) (DPoPE), lipid+addition of CD55 and CD59 blocking antibodies, Rha2-lipid 51, Rha2-lipid 51+CD55 and CD59 blocking antibodies, 14.18-IL2 antibody (positive control), and 14.18-IL@antibody+CD55 and CD59 blocking antibodies. Cells not exposed to lipid and those exposed to the parental ethanolamine lipid remain equally viable in the presence of normal donor serum (serum and DPoPE, respectively). Addition of CD55 and CD59 blocking antibodies has a slight negative impact on cell survival (DPoPE 55 59). Cells treated with antigen-bearing lipid have a large decrease in viability which is significantly amplified by the addition of CD55 and CD59 blocking antibodies. Note that this decrease in viability on combining the Rha2-lipid and CD55 and CD59 blocking antibodies is greater than an additive effect. Buffer-treated cells exposed to 14.18-IL2, an antibody recognizing cell surface GD2 serve as a positive control for active complement. Cell Titer-Glo® assay (Promega) was used to measure living cells, Viability=(luminescence in wells treated with normal serum)/(luminescence of wells treated with heat inactivated serum).

Example 7: Assessing Activation of Cellular Responses

CDC is complement-mediated cytotoxicity. It is an innate, humoral type of immunity that is activated quickly to initiate inflammatory responses and ultimately make holes in the membranes of target cells. For example, this is the pathway active in early stages of hyperacute rejection of xenotransplanted porcine organs. Antibodies that are of the IgM type are very good at activating this pathway. ADCC is antibody dependent cell-mediated cytotoxicity. This is the cellular response involving natural killer cells, granulocytes, macrophages etc. This pathway is mediated by the binding of IgG antibodies to CD16 molecules on effector cells. This is the pathway that has the potential to educate the immune system about cryptic tumor antigens, to attack sites of metastasis, and to create a long-lived memory.

Experiments were performed using the art-recognized Chromium-51 ($^{51}Cr$) release assay to assess if Rha2-lipid conjugate 51 was capable of activating cellular responses ADCC.

M21 cells were treated with lipid as described in Example 6. Target cells are labeled with $^{51}$Cr and the release of label is a measure of cell cytolysis. In this case, the cells were contacted with Na$^{51}$Cr label overnight which is somewhat longer than is typically employed in the assay.

Figure 10:
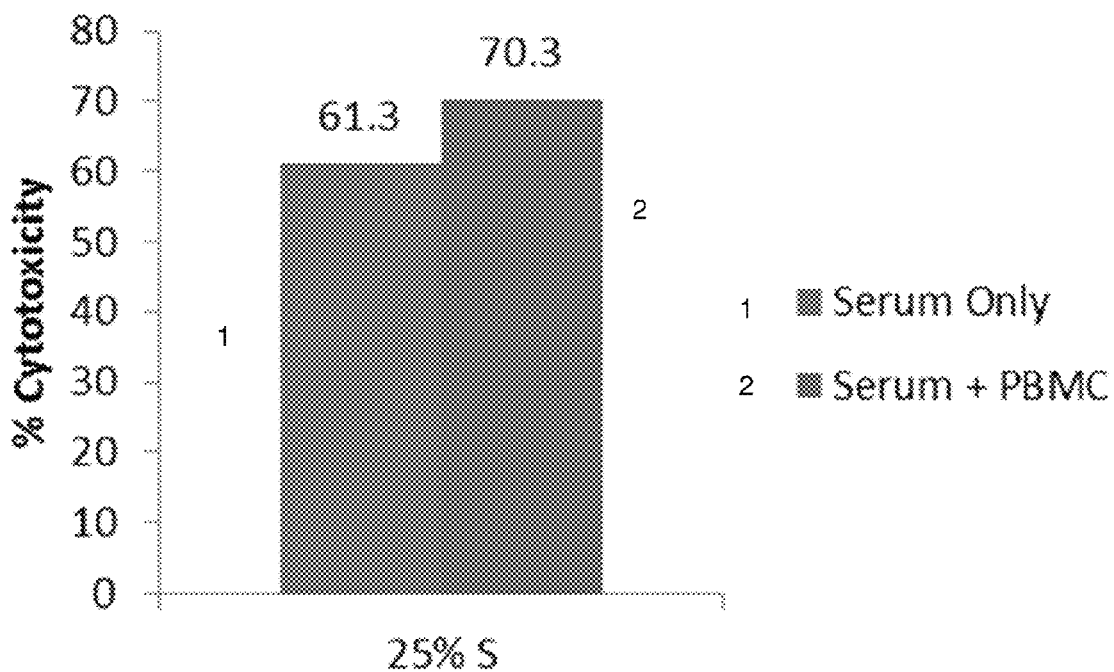
FIG. 10 is a graph showing results of cytotoxicity as assessed in a chromium release assay as described in Example 7. The addition of PBMCs which contain effector cells shows an increase in cytotoxicity.

The results of this assay as illustrated in FIG. 10 (left bar, 1) Cr-51 was released from Rha2-DPoPE-treated cells in the presence of serum alone. This confirms results from Example 6 that Rha2-DPoPE was able to mediate CDC. Peripheral blood mononuclear cells (PBMCs) include immune effector cells some of which express CD16, the most important class of which is natural killer cells. When PBMCs were added along with Rha2-DPoPE, cytotoxicity increased, as illustrated in FIG. 10 (right bar, 2). While the increase observed in this preliminary experiment is relatively small, the results indicate a possible role for cell mediated mechanisms of cell death.

We claim:

1. A lipid conjugate of formula:

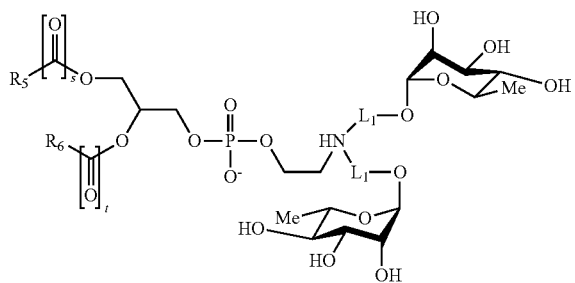

where:
both of s and t are 0, both of s and t are 1, or one of s or t is 0, and the other of s or t is 1;
Me is a methyl group;
$R_5$ and $R_6$ are independently selected from alkyl or monounsaturated alkenyl groups having 12-18 carbon atoms; and
$L_1$ is $-(CH_2)_{a-b}-$, where a+b is 4-6.

2. A pharmaceutical composition comprising a therapeutically effective amount of one or more lipid conjugates of claim 1 and a pharmaceutically acceptable carrier.

3. The pharmaceutical composition of claim 2 further comprising one or more antibodies, and/or one or more antigen lipid conjugates where the antigen is other than L-rhamnose antigen and/or one or more non-conjugated lipids which can facilitate insertion of antigen-lipid conjugates into cell membranes.

4. The pharmaceutical composition of claim 2, wherein the lipid conjugate is formed into a lipid aggregate selected from a vesicle, a bilayer, a micelle, a liposome or a mixture thereof.

5. A method for treating melanoma in an individual in need of treatment thereof and which individual has endogenous anti-rhamnose antibodies which comprises administering a therapeutically effective amount of a lipid conjugate of claim 1 or a pharmaceutical composition comprising said lipid conjugate to a melanoma tumor cell such that the cell is labeled with anti-rhamnose antigen.

6. The method of claim 5, wherein administration comprises intratumoral injection.

7. The method of claim 5, wherein administration is by intradermal injection.

8. A lipid conjugate of claim 1 of formula:

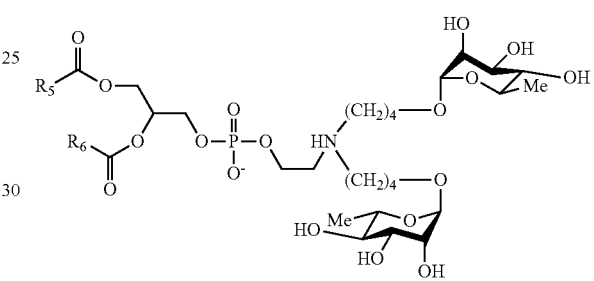

where Me is a methyl group, and $R_5$ and $R_6$ are alkyl or monounsaturated alkenyl groups having 12-18 carbon atoms.

9. The lipid conjugate of claim 8, wherein $R_5$ and $R_6$ are monounsaturated alkenyl groups having 12-18 carbon atoms.

10. The lipid conjugate of claim 9 of formula:

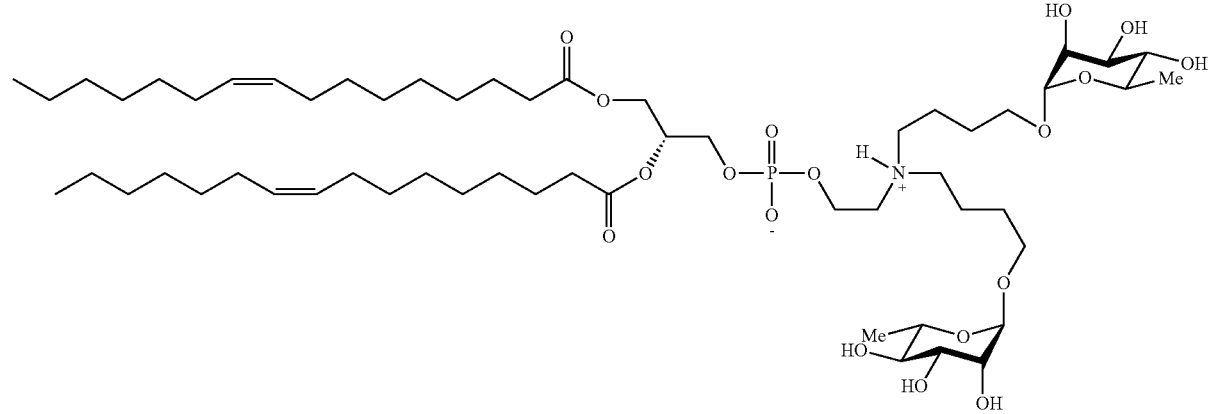

where Me is a methyl group.

11. The lipid conjugate of claim 1, wherein both $L_1$ are $-(CH_2)_4-$.

12. A pharmaceutical composition comprising a therapeutically effective amount of one or more lipid conjugates of claim 8 and a pharmaceutically acceptable carrier.

13. The pharmaceutical composition of claim 12 further comprising one or more antibodies, and/or one or more antigen lipid conjugates where the antigen is other than L-rhamnose antigen and/or one or more non-conjugated lipids which can facilitate insertion of antigen-lipid conjugates into cell membranes.

14. The pharmaceutical composition of claim 13, wherein the lipid conjugate is formed into a lipid aggregate selected from a vesicle, a bilayer, a micelle, a liposome or a mixture thereof.

* * * * *

UNITED STATES PATENT AND TRADEMARK OFFICE
CERTIFICATE OF CORRECTION

PATENT NO. : 9,861,702 B2
APPLICATION NO. : 13/842800
DATED : January 9, 2018
INVENTOR(S) : Laura L. Kiessling et al.

Page 1 of 1

It is certified that error appears in the above-identified patent and that said Letters Patent is hereby corrected as shown below:

In the Claims

At Column 43, Line 41 (Claim 1), replace "—$(CH_2)_{a-b}$—" with -- —$(CH_2)_{a+b}$— --

Signed and Sealed this
Thirty-first Day of July, 2018

Andrei Iancu
*Director of the United States Patent and Trademark Office*